US012745914B2

(12) United States Patent
Everman et al.

(10) Patent No.: US 12,745,914 B2
(45) Date of Patent: Sep. 29, 2026

(54) METHODS AND SYSTEMS FOR DETECTING AN IMMINENT LOSS OF CONSCIOUSNESS

(71) Applicant: GMECI, LLC, Beavercreek, OH (US)

(72) Inventors: Bradford R. Everman, Haddonfield, NJ (US); Brian Scott Bradke, Brookfield, VT (US)

( * ) Notice: Subject to any disclaimer, the term of this patent is extended or adjusted under 35 U.S.C. 154(b) by 0 days.

(21) Appl. No.: 17/732,047

(22) Filed: Apr. 28, 2022

(65) Prior Publication Data

US 2023/0346230 A1 Nov. 2, 2023

(51) Int. Cl.

*A61B 5/0205* (2006.01)
*A61B 5/08* (2006.01)
*A61B 5/11* (2006.01)

(52) U.S. Cl.

CPC .......... *A61B 5/0205* (2013.01); *A61B 5/0816* (2013.01); *A61B 5/11* (2013.01)

(58) Field of Classification Search

CPC ........ A61B 5/0205; A61B 5/0816; A61B 5/11
See application file for complete search history.

(56) References Cited

U.S. PATENT DOCUMENTS 3,572,331 A 3/1971 Kissen
4,775,116 A 10/1988 Klein
H1039 H * 4/1992 Tripp, Jr. ................. 128/202.16
7,082,946 B2 8/2006 Farin et al.
7,383,105 B2 6/2008 Conroy, Jr.
8,164,464 B2 4/2012 Matos
8,517,018 B2 8/2013 Wenzel et al.
8,548,547 B2 10/2013 Vij
9,038,628 B2 5/2015 Ratajczak et al.
9,994,317 B2 6/2018 Sharma
11,235,183 B1 * 2/2022 Dashevsky ............ A61B 5/486
2005/0202375 A1 9/2005 Nevo et al.
2008/0058621 A1 * 3/2008 Melker ................ A61B 5/6817 701/4
2009/0088606 A1 * 4/2009 Cuddihy ................ G16H 40/67 600/300

(Continued)

FOREIGN PATENT DOCUMENTS

CH 702633 A1 8/2011
CN 113616167 A * 11/2021 ......... A61B 5/02028

(Continued)

*Primary Examiner* — John R Downey
(74) *Attorney, Agent, or Firm* — CALDWELL LLC

(57) ABSTRACT

Aspects relate to methods and systems for detecting imminent loss of consciousness. An exemplary system includes at least a respiratory sensor configured to detect a respiration parameter associated with a user, at least a circulatory sensor configured to detect a circulation parameter associated with the user, at least a processor configured to receive the at least a respiration parameter and the at least a circulation parameter, detect a condition associated with the user as a function of the at least a respiration parameter and the at least a circulation parameter, and identify an imminent loss of consciousness event associated with the user as a function of the at least a respiration parameter and the at least a circulation parameter, and at least a user interface configured to alert the user as a function of the imminent loss of consciousness event.

22 Claims, 13 Drawing Sheets

(56) References Cited

U.S. PATENT DOCUMENTS

| | | | | |
|---|---|---|---|---|
| 2013/0281871 | A1* | 10/2013 | White | A61B 5/08 600/529 |
| 2014/0003659 | A1 | 1/2014 | Hoffmann et al. | |
| 2014/0347197 | A1 | 11/2014 | Boomgarden et al. | |
| 2015/0151838 | A1 | 6/2015 | Kerns et al. | |
| 2016/0066808 | A1* | 3/2016 | Hijazi | A61B 5/333 600/382 |
| 2016/0272341 | A1 | 9/2016 | Van Horn et al. | |
| 2017/0351828 | A1* | 12/2017 | Cronin | A61B 5/0205 |
| 2018/0126194 | A1 | 5/2018 | Salin et al. | |
| 2019/0090800 | A1* | 3/2019 | Bosworth | A61B 5/0015 |
| 2019/0167211 | A1* | 6/2019 | Everman | G09B 9/08 |
| 2019/0282839 | A1 | 9/2019 | Wenzel et al. | |
| 2020/0160877 | A1 | 5/2020 | Gauduin et al. | |
| 2020/0215361 | A1 | 7/2020 | Delprat et al. | |

FOREIGN PATENT DOCUMENTS

| | | | |
|---|---|---|---|
| JP | 2962006 | B2 | 10/1999 |
| WO | 2015106202 | | 7/2015 |

* cited by examiner

100

METHODS AND SYSTEMS FOR DETECTING AN IMMINENT LOSS OF CONSCIOUSNESS

FIELD OF THE INVENTION

The present invention generally relates to the field of diagnostics. In particular, the present invention is directed to methods and systems for detecting an imminent loss of consciousness.

BACKGROUND

Presently a number of high stress fields can result in the participants loss of consciousness, for example a pilot of an aircraft, such as fighter plane. Loss of consciousness can result in damage, injury, and even death.

SUMMARY OF THE DISCLOSURE

In an aspect, an exemplary system for detecting imminent loss of consciousness includes at least a respiratory sensor configured to detect a respiration parameter associated with a user, at least a circulatory sensor configured to detect a circulation parameter associated with the user, at least a processor configured to receive the at least a respiration parameter and the at least a circulation parameter, detect a condition associated with the user as a function of the at least a respiration parameter and the at least a circulation parameter, and identify an imminent loss of consciousness event associated with the user as a function of the at least a respiration parameter and the at least a circulation parameter, and at least a user interface configured to alert the user as a function of the imminent loss of consciousness event.

In another aspect, an exemplary method of detecting imminent loss of consciousness includes detecting, using at least a respiratory sensor, a respiration parameter associated with a user, detecting, using at least a circulatory sensor, a circulation parameter associated with the user, receiving, using at least a processor, the at least a respiration parameter and the at least a circulation parameter, detecting, using the at least a processor, a condition associated with the user as a function of the at least a respiration parameter and the at least a circulation parameter, identifying, using the at least a processor, an imminent loss of consciousness event associated with the user as a function of the at least a respiration parameter and the at least a circulation parameter, and alerting, using at least a user interface, the user as a function of the imminent loss of consciousness event.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for detecting an imminent loss of consciousness. In an embodiment, loss of consciousness may be associated with a condition, for example without limitation hypoxia, hypocapnia, and/or G-induced loss of consciousness.

Aspects of the present disclosure can be used to predict an imminent loss of consciousness. Aspects of the present disclosure can also be used to alert a user to an imminent loss of consciousness and instruct the user to perform instructions to prevent loss of consciousness. This is so, at least in part, because system and methods taught herein may differentiate between condition associated with a loss of consciousness and provide specialized auditory coaching as a function of the condition.

Aspects of the present disclosure allow for detected physiological and environmental parameters to be used in determining an imminent loss of consciousness. Exemplary embodiments illustrating aspects of the present disclosure are described below in the context of several specific examples.

Figure 1:
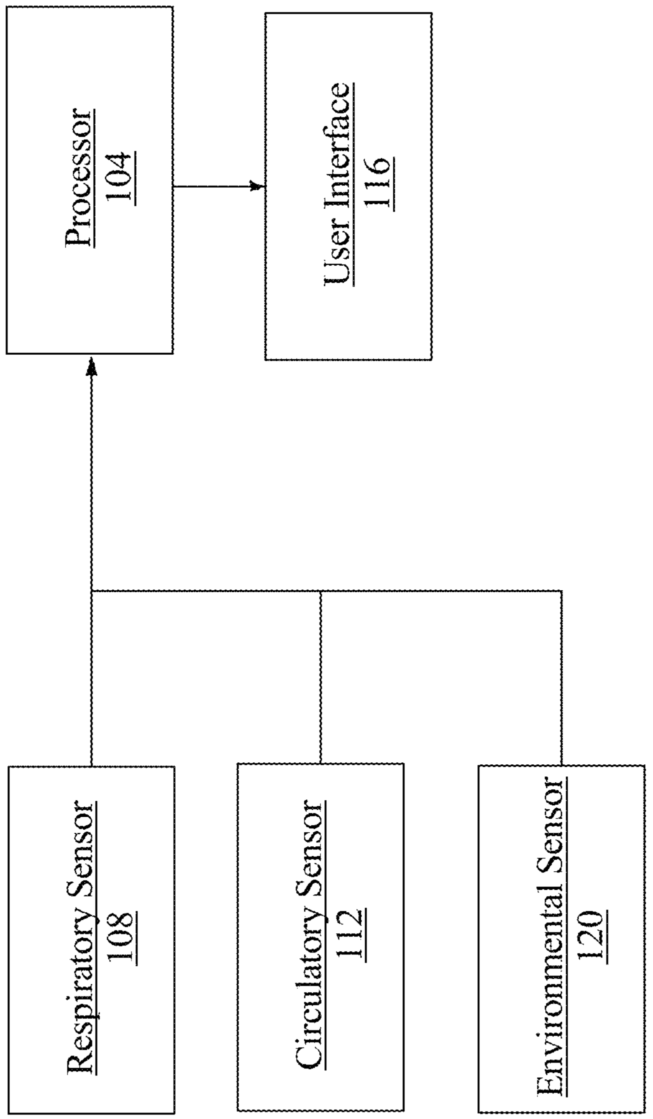
FIG. 1 is a block diagram of an exemplary system for detecting imminent loss of consciousness.

Referring now to FIG. 1, an exemplary embodiment of a system 100 for detecting imminent loss of consciousness is illustrated. System includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of system 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 may include at least a respiratory sensor 108. As used in this disclosure, a "respiratory sensor" is a sensor configured to detect a respiration parameter representative of a phenomenon associated with respiration, for example without limitation respiration of a user. Respiratory sensor 108 may be configured to detect a respiration parameter associated with a user. Respiration sensor 108 may include any sensor described in this disclosure, including without limitation a blood oxygen meter. As used in this disclosure, a "respiration parameter" is at least an element of data representative of a phenomenon associated with respiration, for example without limitation respiration of a user. Respiratory sensor 108 may include any sensor described in this disclosure, including with reference to FIGS. 2-11. In some embodiments, at least a respiratory sensor 108 may include at least an inhalation sensor. As used in this disclosure, a "inhalation sensor" is a sensor configured to detect an inhalation parameter representative of a phenomenon associated with inhalation, for example without limitation inhalation of a user. Inhalation sensor may include any inhalation sensor described in this disclosure. In some cases, inhalation sensor may include an inspirate sensor. In some embodiments, at least a respiratory sensor 108 may include at least an exhalation sensor. As used in this disclosure, a "exhalation sensor" is a sensor configured to detect an exhalation parameter representative of a phenomenon associated with exhalation, for example without limitation exhalation of a user. An exemplary non-limiting respiration parameter includes blood oxygen level SpO2.

With continued reference to FIG. 1, system 100 may include at least a circulatory sensor 112. As used in this disclosure, a "circulatory sensor" is a sensor configured to detect a circulation parameter representative of a phenomenon associated with blood circulation, for example without limitation blood circulation of a user. Circulatory sensor 112 may be configured to detect a circulation parameter associated with user. A circulation sensor 112 may include any sensor described in this disclosure, including without limitation a pulse rate meter. As used in this disclosure, a "circulation parameter" is at least an element of data representative of a phenomenon associated with blood circulation, for example without limitation blood circulation of a user. Circulatory sensor 112 may include any sensor described in this disclosure, including with reference to FIGS. 2-11. In some embodiments, circulatory sensor 112 may include a near-infrared spectroscopy sensors. An exemplary non-limiting circulation parameter includes pulse rate.

With continued reference to FIG. 1, system 100 may include at least a user interface 116. As used in this disclosure, a "user interface" is a system that is designed and/or configured to facilitate communication between at least a system, such as without limitation a processor, and a user by way of at least an output communicated to the user and/or at least an input communicated from the user. Exemplary non-limiting user interfaces 116 include displays, audio systems, haptic systems, head mounted displays, mice, joysticks, keyboards, and the like. User interface 116 may be configured to alert the user as a function of the imminent loss of consciousness event. In some cases, user interface 116 may include headphones, for example over ear headphones including an earcup. In some cases, user interface may include a bone conducting transducer, for example located within an earcup of a headphone. A "bone-conducting transducer," as used in this disclosure, is a device or component that converts an electric signal to a vibrational signal that travels through bone in contact with the device or component to an inner ear of user, which interprets the vibration as an audible signal. Bone-conducting transducer may include, for instance, a piezoelectric element, which may be similar to the piezoelectric element found in speakers or headphones, which converts an electric signal into vibrations. In an embodiment, bone-conducting transducer may be mounted to housing in a position placing it in contact with a user's bone; for instance, where housing includes or is incorporated in an ear cup, housing may place bone-conducting transducer in contact with user's skull just behind the ear, over the sternocleidomastoid muscle. Likewise, where housing includes a headset, mask, or helmet, housing may place bone-conducting transducer in contact with a portion of user's skull that is adjacent to or covered by headset, mask, or helmet. Additional disclosure related to headphones and bone conducting transducers may be found in U.S. patent application Ser. No. 16/859,483 filed on Apr. 27, 2020, entitled "HUMAN PERFORMANCE OXYGEN SENSOR," the entirety of which is incorporated herein by reference.

Still referring to FIG. 1, in some embodiments, at least a user interface 116 may include an audio system. As used in this disclosure, an "audio system" is a system that is configured to transduce a signal to sound and/or vice versa. Non-limiting exemplary audio systems include loudspeakers, headphones, microphones, bone-conducting transducers, and the like. In some cases, at least a user interface 116 may be configured to generate auditory coaching to user, for instance as a function of imminent loss of consciousness event. As used in this disclosure, "auditory coaching" is audio instructions intended for a user to listen and respond to. Auditory coaching may be selected based upon condition. For example, different auditory coaching may be selected for G-induced loss of consciousness, hypocapnia, hypoxia, and the like. Auditory coaching may include any instructions to avoid an imminent loss of consciousness event described in this disclosure, including those described in detail below.

Still referring to FIG. 1, in some embodiments, system 100 may include an environmental sensor 120. As used in this disclosure, an "environmental sensor" is a sensor configured to detect an environmental parameter representative of a phenomenon associated with an environment, for example without limitation an environment within which a user is in such as a vehicle cabin. Environmental sensor 120 may include any sensor described in this disclosure, including for example an inertial measurement unit, a gas sensor, and the like. Environmental sensor 120 may be configured to detect an environmental parameter associated with an environment of user. As used in this disclosure, a "environmental parameter" is at least an element of data representative of a phenomenon associated with an environment, for example without limitation an environment within which a user is in such as a vehicle cabin. In some embodiments, environmental sensor 120 may include a motion sensor. As used in this disclosure, a "motion sensor" is a sensor configured to detect a motion parameter representative of a phenomenon associated with motion, for example without limitation motion of a user an/or vehicle. Non-limiting exemplary motion sensors include inertial measurement units, accelerometers, gyroscopes, and the like. In some cases, at least a motion sensor may be configured to detect at least a motion parameter. As used in this disclosure, a "motion parameter" is at least an element of data representative of a phenomenon associated with motion, for example without limitation motion of a user and/or a vehicle. In some cases, at least a processor 104 may be further configured to receive at least a motion parameter; detect condition as a function of the at least a motion parameter; and identify an imminent loss of consciousness event as a function of the at least a motion parameter.

With continued reference to FIG. 1, processor 104 may be in communication with at least a respiratory sensor 108 and/or a circulatory sensor 112. Processor 104 may receive at least a respiration parameter and/or at least a circulation parameter, for example by way of one or more signals. Processor 104 may detect a condition associated with user as a function of at least a respiration parameter and/or at least a circulation parameter. As used in this disclosure, a "condition" is user state which a user is currently in or may be at risk of developing in the near future. Exemplary non-limiting conditions include hypoxia, G-induced loss of consciousness, hypocapnia, and the like. Processor 104 may identify an imminent loss of consciousness event associated with user as a function of at least a respiration parameter and/or at least a circulation parameter. As used in this disclosure, an "imminent loss of consciousness event" is a prediction that a user is reasonably likely to experience loss of consciousness in the near future (e.g., within fractions of a second, within seconds, and/or within minutes). An imminent loss of consciousness event may occur as a result of one or more conditions, including without limitation hypoxia, G-induced loss of consciousness, hypocapnia, and the like. As used in this disclosure, "G-induced loss of consciousness (GLOC)" is a loss of consciousness occurring from excessive and sustained g-forces. In some cases, g-forces may drain blood away from a user's brain causing cerebral hypoxia and GLOC. As used in this disclosure, "hypoxia" is a condition in which a body or a region of the body is deprived of adequate oxygen supply. In some cases, hypoxia may be classified as either generalized, affecting the whole body, or local affecting a region of the body. As used in this disclosure, "hypocapnia" also referred to as "hypocarbia" is a condition of reduced carbon dioxide in blood. In some cases, hypocapnia may result from deep and/or rapid breathing, often known as hyperventilating. Detecting of condition and/or identifying imminent loss of consciousness may be performed according to any algorithm and/or machine-learning process described in this disclosure, for instance those described below in detail.

With continued reference to FIG. 1, in some embodiments, one or more of detection of a condition and/or identification of an imminent loss of consciousness event may include trend rate analysis. As used in this disclosure, "trend analysis" is an analysis technique that attempts to identify a trend within data. In some cases, trend analysis may be used to predict a trend associated with data, so that deviations from the trend, for example in a current parameter value, may be determined. Trend analysis may include, without limitation, moving averages, exponentially weighted moving averages, moving average converging/diverging, trend percentage calculation, regression analysis, trend estimation, Mann-Kendall test, Kendall rank correlation, smoothing, and the like.

With continued reference to FIG. 1, in some embodiments, at least a circulation parameter, e.g., pulse rate, and/or at least a respiratory parameter, e.g., blood oxygen level (SpO2), may be analyzed according to trend analysis. For example, an exponentially weighted moving average (EMA) of at least a parameter may be calculated thus:

$$EMA_n = \frac{2}{1+\lambda} * (x_n - x_{n-1}) + EMA_{n-1}$$

where, $EMA_n$ is a current exponentially weighted moving average value, $\lambda$ is a weighting factor, $x_n$ is a current parameter value, $x_{n-1}$ is a preceding parameter value, and $EMA_{n-1}$ is a preceding exponentially weighted moving average value. Weighting factor in some cases influences an EMA response, such that larger weighting factors correspond to longer EMAs (e.g., short term trends and/or long term trends) with a slower response to changing values. In some cases, different parameters may have different desired durations (i.e., terms) associated with trend analysis. For example, an SpO2 parameter may have a long trend of about 60 seconds and a short trend of about 15 seconds. Likewise, a pulse rate may have a long trend of about 600 seconds and a short trend of about 300 seconds.

With continued reference to FIG. 1, in some embodiments, trend analysis may include determining a moving average converging/diverging (MACD) value. MACD may represent changes in a parameter's propensity to follow a trend. In some cases, MACD may be a function of a short term trend and a long term trend. For example MACD may be determine according to:

$$MACD=EMA_{short}-EMA_{long}$$

Within context of MACD in this disclosure, "convergence" refers to MACD becoming smaller over time, as a difference between short term and long term trends diminishes. Within context of MACD in this disclosure, "divergence" refers to MACD becoming larger over time, as a difference between short term and long term trends increases.

With continued reference to FIG. 1, in some embodiments, trend analysis may include finding a trend of MACD value. For example, a divergence trend may be found thus $$\text{Divergence}_n = \frac{2}{1+\lambda} * (MACD_n - MACD_{n-1}) + \text{Divergence}_{n-1}$$

such that, when divergence trend is higher than MACD, there is an increasing trend in the underlying parameter; and when the divergence trend is lower than the MACD, there is a decreasing trend. In some cases, magnitude of MACD may represent a relative magnitude of a trend. A higher value means may indicate that a given parameter is increasing/decreasing faster, i.e., more dramatically, than a lower MACD. In some embodiments, MACD may be used to filter out physiologically normal changes in physiological parameters (e.g., circulation parameters and/or respiratory parameters) versus changes in physiological parameters that are indicative of a condition and/or an imminent loss of consciousness event.

With continued reference to FIG. 1, in some embodiments, processor 104 may be configured to delay alerts for a predetermined time. For instance, in some cases, processor 104 may wait a certain amount of time (e.g., 20 seconds, 40 seconds, 60 seconds, and the like) after initialization before arming the system 100 to alert user. In some cases, this will prevent erroneous alerting while sensors 108, 112, and 120 are placed.

With continued reference to FIG. 1, in some embodiments, processor 104 may perform one or more of detecting a condition and/or identifying an imminent loss of consciousness event by way of one or more algorithms. Exemplary algorithms are provided below in greater detail. In some cases, processor 104 may configured to operate multiple algorithms, some or all of these algorithms may be user. In some cases, one or more particular algorithms may be selected, for example by way of user interface 116. In some cases, one or more settings associated with algorithms may, likewise, be selected, for example by way of user interface 116. Exemplary non-limiting settings may include thresholds, time-delays, debounces, and the like. In some cases, authentication may be required prior to adjusting settings.

With continued reference to FIG. 1, in some cases, processor 104 may be configured to perform a threshold algorithm. For example, in some cases, processor 104 may compare one or more parameters to at least a preset threshold and/or at least a preset range. In some exemplary embodiments, a value representing one or more of at least a circulation parameter and/or at least a respiratory parameter is found to be outside of at least a preset range for at least a predetermined period of time, processor 104 may detect a condition and/or indicate an imminent loss of consciousness event. In some embodiments, processor 104 may use a plurality of preset thresholds and/or preset ranges. For example in some cases a first threshold may be used to indicate a potential presence or future presence of a condition and a second threshold may be used to indicate an imminent loss of consciousness event.

With continued reference to FIG. 1, in some cases, processor 104 may be configured to compare parameter values against a baseline. For example, in some cases, a preset threshold and/or preset range may be determined by processor 104 according to historical data (e.g., baseline), for example historical data related to user. For example, in a case where a first respiratory sensor registers "normal" as SpO2=90%, where a second respiratory sensor registers SpO2=98% as "normal." Thresholds may be set to a 10% decrease from "normal." In this case, user may receive an alert if a either sensor detects decrease of 10% from their baseline (80% first sensor, 88% second sensor).

With continued reference to FIG. 1, in some cases, processor 104 may be configured to perform an algorithm as a function of both at least a respiration parameter and at least a circulation parameter. For instance, in some cases, one or more of a condition and an imminent loss of consciousness event may be identified as a function of a SpO2 and pulse rate. For example, a decreased SpO2 and a precipitous increase in pulse rate, for example as indicated by trend analysis, may be indicative of an imminent loss of consciousness event. According to an exemplary algorithm an imminent loss of consciousness event may be identified according to a following algorithm. (1) If SpO2 FastEMA is less than a first threshold AND Pulse Rate MACD signal is Positive AND counter timeout is greater than timeout threshold (e.g., 5 seconds), then a first alert may be generated. In some cases, first alert may have a first sound alert level, for example 2 beeps per second @2000 Hz. (2) If the conditions of (1) are met and SpO2 FastEMA is less than a second threshold, then a second alert may be generated. In some cases, second alert may have a second sound alert level, for example 4 beeps per second @2000 Hz. (3) If the conditions of (1) are met and SpO2 FastEMA is less than a third threshold, a third alert may be generated. In some cases, third alert may have a third sound alert level, for example 8 beeps per second @2000 Hz. In some cases, there may be a time delay, e.g., debounce and/or hysteresis, associated with changing from one alert level to another. As a non-limiting example, in some cases, there may be no time delay when advancing from one alert level to a higher alert level, but there may be a 5-second delay when going from a higher alert level to a lower alert level.

With continued reference to FIG. 1, in some embodiments, a G-induced loss of consciousness condition may be determined with or without an imminent loss of consciousness as a function of at least a motion parameter, at least a circulation parameter, and at least a respiration parameter. In some cases, at least a motion parameter may include acceleration of user and/or vehicle. In some cases, at least a circulation parameter may include pulse rate. In some cases, at least a respiration parameter may include blood oxygen level (SpO2). In some cases, blood oxygen level may be measured at a posterior auricular artery (i.e., behind an ear). Posterior auricular artery may connect carotid to brain and thereby provide a desirable location for measuring blood oxygenation within context of hypoxia. In some cases, a pilot may experience high G-loads and a decrease in blood flow to the brain. In some cases, system 100 may identify an imminent loss of consciousness and a predictive warning of GLOC. In some cases, system 100 may generate auditory coaching in response to GLOC. Auditory coaching may include instructions for user to perform one or more of anti-G straining maneuvers (AGSMs), change breathing/air exchange timing, and/or alter control of vehicle to reduce Gs. Auditory coaching may include instructions for AGSM. AGSM may include one or more of isometrically contracting lower body and/or abdomen muscles, for instance while relaxing shoulders. forceful deliberate breathing (air exchange), for example short bursts every 3 seconds, and increasing consciously intrapleural pressure in between breaths, for example to improve cardiac function and cranial blood pressure.

With continued reference to FIG. 1, in some embodiments, a hypocapnia condition may be determined with or without an imminent loss of consciousness as a function of at least a respiration parameter and at least a circulation parameter. Hypocapnia, or reduced CO2 in blood, in some cases, may be caused by hyperventilation characterized by shallow, rapid respiration. In some cases, system 100 may use respiration parameters, for example from at least a respiratory sensor, such as an inhalation sensor and/or an exhalation sensor, to detect decreasing CO2 levels and increased respiration rates. In some cases, system 100 may use these parameters with or without circulation parameter to detect hypocapnia. In some cases, system 100 may generate auditory coaching in response to hypocapnia. Auditory coaching may include instructions to user to slow their respiration rate, and to breathe deeper and slightly slower than normal.

Still referring to FIG. 1, in some embodiments, a user may eliminate, disarm, or otherwise silence an alert. In some cases, a user may remove an alert by correcting a physiological problem, e.g., change SpO2 and/or pulse rate. For example, in some cases, user may breathe more oxygen or refrain from high G maneuvers. Alternatively or additionally, in some cases user may silence an alert by way of at least a user interface 116.

Still referring to FIG. 1, in some embodiments, one or more of at least a respiratory sensor 108, at least a circulatory sensor 112, and/or at least an environmental sensor 120 may include a plurality of sensors. In some cases, a plurality of sensors may include at least a master sensor configured to detect at least a master parameter and at least a slave sensor configured to detect at least a slave parameter. As used in this disclosure, a "master" is an attributive which describes a particular component of a plurality of component, where the particular, master, component is prioritized over and/or controls other (slave) components within the plurality of components. As used in this disclosure, a "slave" is an attributive which describes at least a particular component of a plurality of components, where the at least a particular, slave, component is posterioritized after and/or controlled by another (master) device within the plurality of components. Processor 104 may receive at least a master parameter and at least a slave parameter. Processor 104 may merge at least a parameter as a function of at least a master parameter and at least a slave parameter. For example, in some cases, system 100 may additionally include a master circulatory sensor configured to detect a master circulation parameter; and a slave circulatory sensor configured to detect a slave circulation parameter; and wherein, at least a processor 104 may be further configured to merge at least a circulation parameter as a function of the master circulation parameter and the slave circulation parameter.

Still referring to FIG. 1, in some cases, merging master and slave parameters and/or any plurality of parameters may include comparing a difference between the parameters, such as without limitation a percent difference. In some cases, a difference between parameters may be calculated thus:

$$\frac{\text{Master} - \text{Slave}}{(\text{Master} + \text{Slave})^2}$$

According to the above equation, a negative number means slave parameter was higher than master and vice versa In some cases, merging may include filtering one or more parameters having bad data, such as without limitation out of range parameters. For example, if a parameter is out of range, it may not be included in merging or any other processes. In some cases, a parameter may be determined to have bad data if it does not exhibit an appropriate amount of variability, for example over time. For example, referring to a circulatory parameter, suspected bad data may include an SpO2 value "pegged at 100%" with no variability, "normal" levels sustained below 92% under "normal" conditions. In some embodiments, SpO2 on room air at sea level should be between 92% and 100%, with some variability observed, i.e. the SpO2 should bounce around between 97-99 primarily. SpO2 values that behave differently may be suspected of having bad data. If a parameter is determined to have bad data, corresponding sensor 108, 112, and/or 120 may be flagged. According to some embodiments, bad data detecting and sensor flagging may be performed in situ and/or prior to use of system 100.

Still referring to FIG. 1, in some cases, merging parameters may include averaging. In some cases, merging parameters may be performed as a function of difference between parameters. For example, in some cases, parameters may only be merged when the plurality of parameters have a difference no greater than a certain threshold (e.g., 20%, 10%, 5%, 1%, and the like). In some cases, a parameter from a plurality of parameters may not be merged but may simply be selected for use. For example, in some embodiments, at initialization a used parameter value may be set equal to master parameter value.

Still referring to FIG. 1, in an exemplary embodiment, a circulation parameter, pulse rate, may be selected for use from a plurality of parameters according to a following sequence. (1) a default pulse rate may be set to master pulse rate. (2) If percent difference between master pulse rate and at least a slave pulse rate is greater than a certain threshold (e.g., 20%), then do not merge the parameters and instead select a parameter depending upon parameter value. For example, if the higher pulse rate is less than 180 BPM, use the higher pulse rate, otherwise use the lower pulse rate. (3) If a pulse rate has bad data, use another pulse rate without bad data. In some cases, pulse rate is not merged, instead a single circulatory sensor 112 may be used to provide pulse rate, until the pulse rate is found to possess bad data and another circulatory sensor 112 may be user. Any parameter described in this disclosure may be represented as a signal.

Still referring to FIG. 1, As used in this disclosure, a "signal" is any intelligible representation of data, for example from one device to another. A signal may include an optical signal, a hydraulic signal, a pneumatic signal, a mechanical, signal, an electric signal, a digital signal, an analog signal and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

Still referring to FIG. 1, in some cases, system 100 may perform one or more signal processing steps on a sensed characteristic. For instance, system 100 may analyze, modify, and/or synthesize a signal representative of at least a parameter in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

Figure 2:
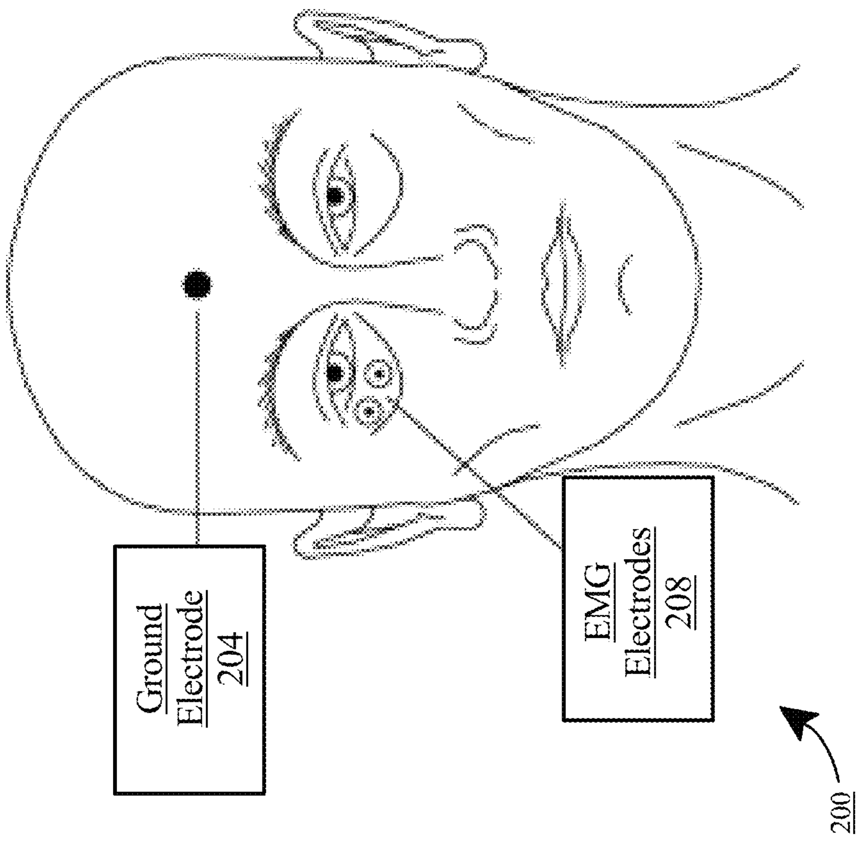
FIG. 2 illustrates exemplary placement of an electromyography sensor.

In some embodiments one or more of at least a respiratory sensor 108 and/or at least a circulatory sensor 112 may include an electromyography (EMG) sensor. Referring now to FIG. 2 an exemplary EMG sensor 200 is illustrated. In some cases, electromyography (EMG) may be an electrodiagnostic medicine technique for evaluating and recording electrical activity produced by skeletal muscles. EMG may be performed using an instrument called an electromyograph to produce a record called an electromyogram. An electromyograph may detect electric potential generated by muscle cells, for instance when these cells are electrically or neurologically activated. Resulting electromyographic signals can be analyzed to detect medical abnormalities, activation level, or recruitment order, or to analyze the biomechanics of human or animal movement. In some cases, EMG may also be used as middleware in gesture recognition towards allowing input of physical action to a computing device or as a form of human-computer interaction. In some cases, an EMG sensor 200 may be located about an eye of a user and used to detect eye movements and/or blinks, for instance through detection of electrical activity of extraocular muscles. An EMG sensor 200 may include at least a ground electrode 204 and at least an EMG electrode 208. In some cases, a ground electrode 204 may be placed substantially away from an eye and/or extraocular muscles. In some cases, a ground electrode 204 may be electrically isolated (i.e., floating), thereby allowing detection of muscular electrical activity relative the body rather than relative a ground or other reference. In some cases, EMG signals may be substantially made up of superimposed motor unit action potentials (MUAPs) from several motor units (e.g., muscles). EMG signals can be decomposed into their constituent MUAPs. MUAPs from different motor units tend to have different characteristic shapes, while MUAPs recorded by the same electrode from the same motor unit are typically similar. Notably MUAP size and shape depend on where the electrode is located with respect to muscle fibers and so can appear different if an electrode 204, 208 moves position. EMG decomposition may involve any signal processing methods described in this disclosure, including those below.

With continued reference to FIG. 2, in some case EMG signal rectification may include translation of a raw EMG signal to a signal with a single polarity, for instance positive. In some cases, rectifying an EMG signal may be performed to ensure the EMG signal does not average to zero, as commonly a raw EMG signal may have positive and negative components. According to some embodiments, substantially two types of EMG signal rectification may be used full-wave and half-wave rectification. As used in this disclosure, "full-wave rectification" may add EMG signal below a baseline to the EMG signal above the baseline, thereby resulting in a conditioned EMG signal that is all positive. For example, if baseline of EMG signal is zero, full-wave rectification would be equivalent to taking an absolute value of the EMG signal. According to some embodiments, full-wave rectification may conserve substantially all of EMG signal energy for analysis. As used in this disclosure, "half-wave rectification" discards a portion of EMG signal below baseline. As a result of half-wave rectification, average of EMG signal may no longer be zero;

therefore, an EMG signal conditioned by half-wave rectification can be used in further statistical analyses.

Still referring to FIG. 2, in some embodiments, EMG sensor 200 may be used to detect a gaze of user and/or the gaze of the user over time. As used in this disclosure, "gaze" is a direction a user is looking. As used in this disclosure "gaze vector" is a directional vector having a point located at a user's eye (e.g., pupil, retina, or the like) which represents a gaze of the user. In some cases, an EMG sensor 200 may be used to detect a gaze of a user over time and this information may be used as input for one or more machine-learning models described herein. For example, in some cases, user's whose gave is infrequently directed at display may be found to have a relatively lower attentiveness than those whose gaze is fixed on the display. Alternatively or additionally, in some cases, a user's blink rate as detected by EMG sensor 200 may be used as an input for one or more machine-learning described herein. This is because, it also may be that users who blink more frequently are less attentive (e.g., drowsier) than those who blink less. For example, in an extreme case a user whose eyes are closed for prolonged periods of time may be found to be inattentive, perhaps even asleep; this condition may, in some cases, result in a change in an environmental parameter and/or a display parameter in order to wake up the user.

Referring again to FIG. 1, in some embodiments, similar gaze tracking and/or blink tracking functionality may be performed by a user facing camera. In some embodiments, one or more of respiratory sensor 108, circulatory sensor 112, and/or environmental sensor 120 may include at least a camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object. In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively where "image" is used as a verb, in this disclosure, it refers to generation and/or formation of an image. In some embodiments, system 100 may include a machine vision system that includes or is operatively connected to at least a camera. A machine vision system may use images from at least a camera, to make a determination about a scene, space, user and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and $\phi$ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure. An exemplary machine vision camera that may be included as at least a sensor 108 is an OpenMV Cam H7 from OpenMV, LLC of Atlanta, Georgia, U.S.A. OpenMV Cam comprises a small, low power, microcontroller which allows execution of machine vision applications. OpenMV Cam comprises an ARM Cortex M7 processor and a 640×480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detection motion, for example by way of frame differencing algorithms; marker detection, for example blob detection; object detection, for example face detection; eye tracking; person detection, for example by way of a trained machine learning model; camera motion detection, for example by way of optical flow detection; code (barcode) detection and decoding; image capture; and video recording. In some cases, data from a machine vision camera may be used as input for one or more machine-learning models which output one or more of an environmental parameter and a display parameter. In some embodiments, at least a camera may include at least a stereo-camera. As used in this disclosure, a "stereo-camera" is a camera that senses two or more images from two or more vantages. As used in this disclosure, a "vantage" is a location of a camera relative a scene, space and/or object which the camera is configured to sense. In some cases, a stereo-camera may determine depth of an object in a scene as a function of parallax. As used in this disclosure, "parallax" is a difference in perceived location of a corresponding object in two or more images. An exemplary stereo-camera is TaraXL from e-con Systems, Inc of San Jose, California. TaraXL is a USB 3.0 stereo-camera which is optimized for NVIDIA® Jetson AGX Xavier™/Jetson™ TX2 and NVIDIA GPU Cards. TaraXL's accelerated Software Development Kit (TaraXL SDK) is capable of doing high quality 3D depth mapping of WVGA at a rate of up to 60 frames per second. TaraXL is based on MT9V024 stereo sensor from ON Semiconductor. Additionally, TaraXL includes a global shutter, houses 6 inertial measurement units (IMUs), and allows mounting of optics by way of an S-mount lens holder. TaraXL may operate at depth ranges of about 50 cm to about 300 cm.

Still referring to FIG. 1, in some embodiments, a user's position, habiliment, and/or posture may be detected by one or more of at least a respiratory sensor 108, at least a circulatory sensor 112, and at least an environmental sensor 120. For example, in some cases, a machine vision camera, like that described above may be employed to perform the detection. Alternatively or additionally, in some cases, range-imaging or 3D camera may be used for this purpose. An exemplary range-imaging camera that may be included as an at least a sensor 108 is Intel® RealSense™ D430 Module, from Intel® of Mountainview, California, U.S.A. D430 Module comprises active infrared (IR) illumination and a stereoscopic camera, having global shutters and frame rate of up to 90 fps. D430 Module provide a field of view (FOV) of 85.2° (horizontal) by 58° (vertical) and an image resolution of 1280×720. Range-sensing camera may be operated independently by dedicated hardware, or, in some cases, range-sensing camera may be operated by a computing device. In some cases, range-sensing camera may include software and firmware resources (for execution on hardware, such as without limitation dedicated hardware or a computing device). D430 Module may be operating using software resources including Intel® RealSense™ SDK 2.0, which include opensource cross platform libraries. In some cases, data from a range-imaging camera may be used as input for one or more machine-learning models which output one or more of a respiratory parameter, a circulatory parameter, and/or an environmental parameter.

Figure 3:
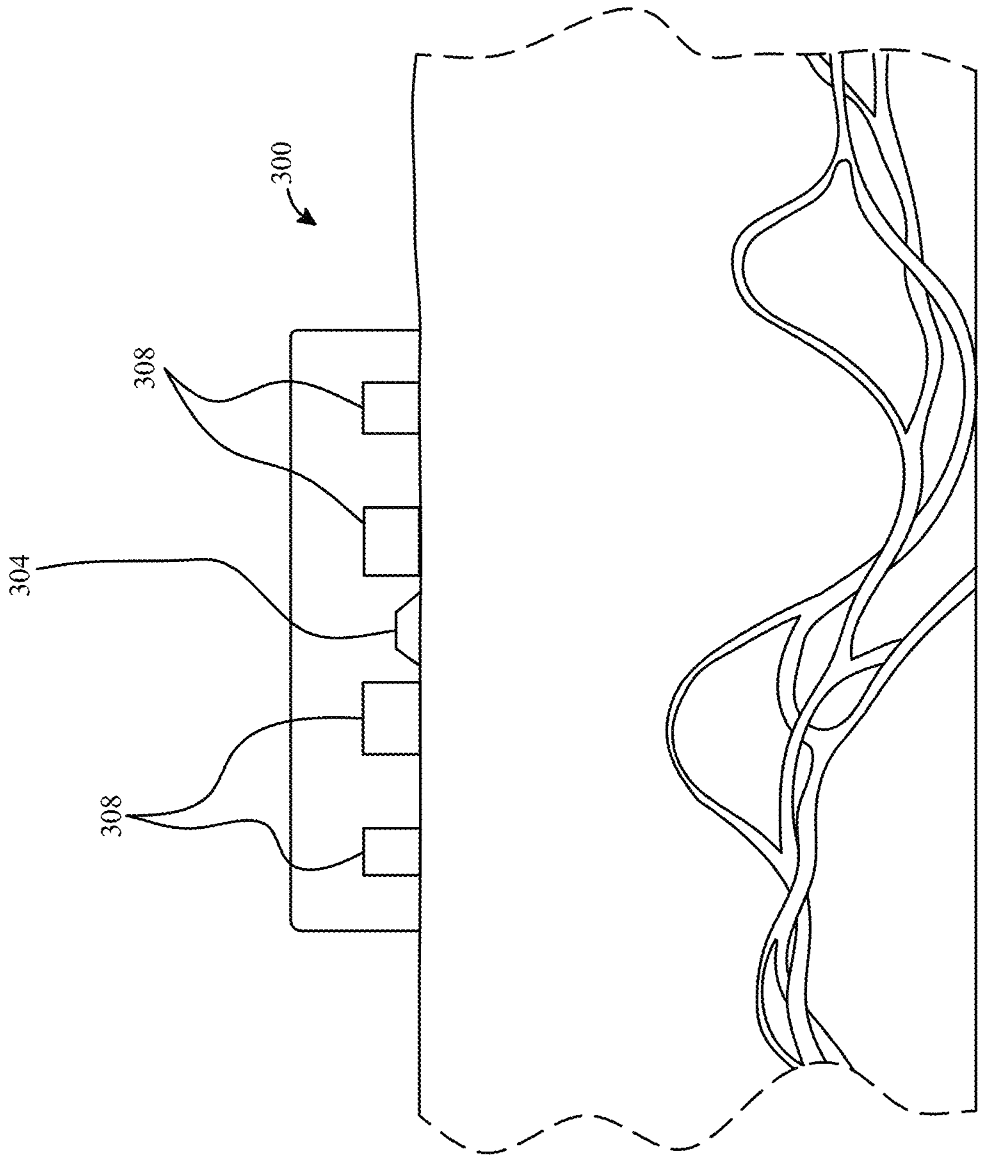
FIG. 3 is a schematic illustration of an exemplary embodiment of a near-infrared spectroscopy sensor.

Still referring to FIG. 1, in some cases one or more of at least a respiratory sensor 108, circulatory sensor 112, and at least an environmental sensor 120 may include an optical sensor, which detects light emitted, reflected, or passing through human tissue. Optical sensor may include a near-infrared spectroscopy sensor. A "near-infrared spectroscopy sensors (NIRS)", as used herein, is a sensor that detects signals in a near-infrared electromagnetic spectrum region, having wavelengths between 780 nanometers and 2,500 nanometers. FIG. 3 illustrates an exemplary embodiment of a NIRS 300 against an exterior body surface, which may include skin. NIRS 300 may include a light source 304, which may include one or more light-emitting diodes (LEDs) or similar element. Light source 304 may, as a non-limiting example, convert electric energy into near-infrared electromagnetic signals. Light source 304 may include one or more lasers. NIRS 300 may include one or more detectors 308 configured to detect light in the near-infrared spectrum. Although the wavelengths described herein are infrared and near-infrared, light source 304 may alternatively or additionally emit light in one or more other wavelengths, including without limitation blue, green, ultra-violet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation CO2 saturation levels, state of hemoglobin as opposed to blood oxygen saturation generally. One or more detectors 308 may include, without limitation, charge-coupled devices (CCDs) biased for photon detection, indium gallium arsenide (InGaAs) photodetectors, lead sulfide (PbS) photodetectors, or the like. NIRS 300 may further include one or more intermediary optical elements (not shown), which may include dispersive elements such as prisms or diffraction gratings, or the like. In an embodiment, NIRS 300 may be used to detect one or more circulatory parameters, which may include any detectable parameter further comprises at least a circulatory parameter. One or more of at least a respiratory sensor 108, circulatory sensor 112, and at least an environmental sensor 120 may include at least two sensors mounted on opposite sides of user's cranium, for example in a master and slave arrangement. Further disclosure related to NIRS sensor may be found in U.S. patent application Ser. No. 16/859,483, entitled "SYSTEMS AND METHODS FOR MEASURING PHYSIOLOGICAL PARAMETERS," the entirety of which is incorporated herein by reference.

Figure 4:
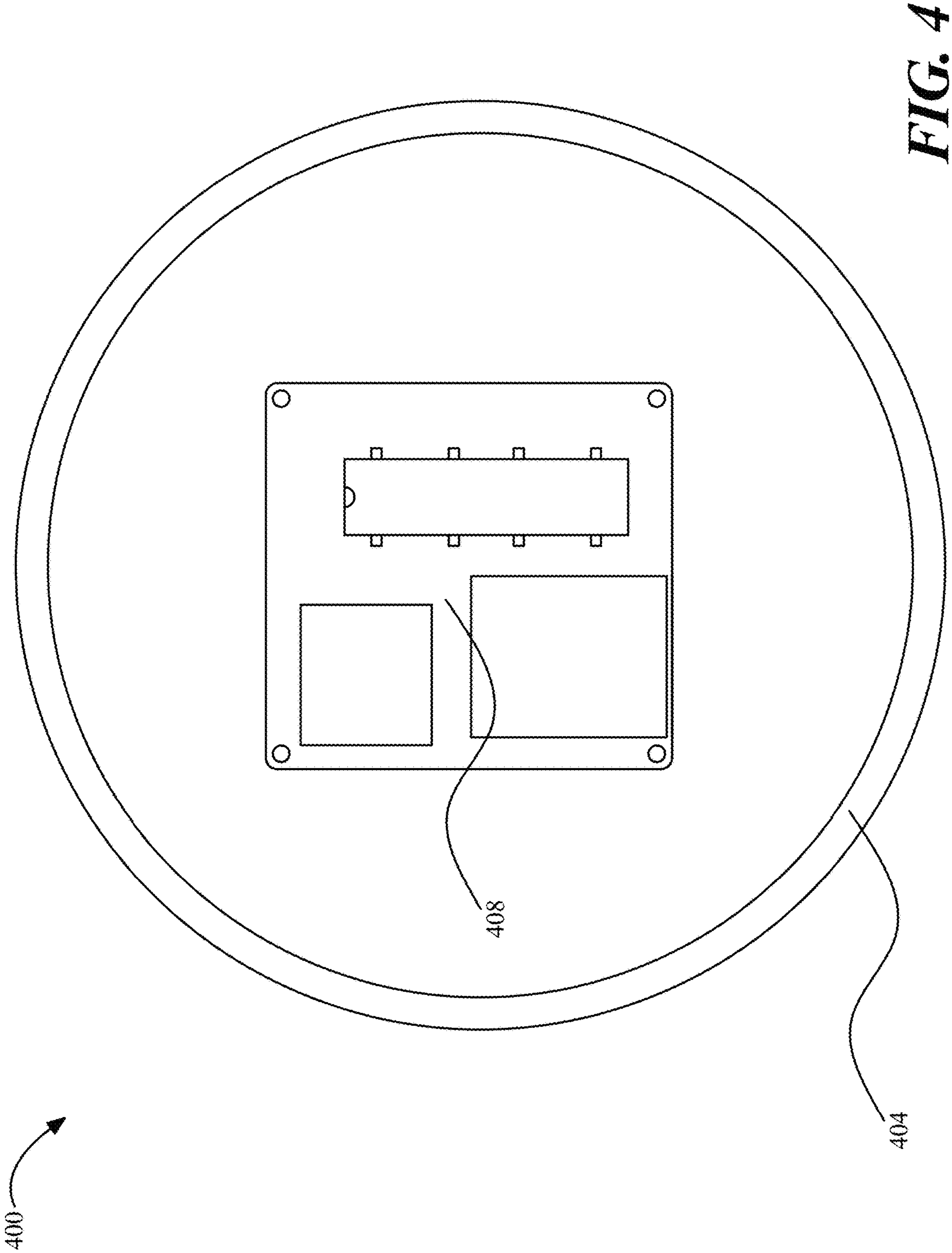
FIG. 4 is a schematic diagram illustrating an exemplary embodiment of a combined exhaled air and environmental gas sensor apparatus.

In some cases, one or more of at least a respiratory sensor 108, circulatory sensor 112, and at least an environmental sensor 120 may include an exhaled gas sensor and/or an environmental gas sensor. Referring now to FIG. 4, combined exhaled air and environmental gas sensor 408 apparatus 400 for mobile respiratory equipment is illustrated. Apparatus 400 includes a housing 404, within which one or more electronic components are positioned. One or more electric components include a sensor 408. Housing 404 may be constructed of any suitable material or combination of materials, including without limitation metal, metal such as aluminum, titanium, steel, or the like, plant materials including bamboo and/or wood, polymer materials such as polycarbonate, polymethyl methacrylate, acrylonitrile butadiene styrene (ABS), or the like, synthetic fibers such as carbon fiber, silicon carbide fiber, metallic fiber, or the like, composite materials such as fiberglass, laminated fiberglass, plywood, or the like, or any combination of the above. Housing 404 may be manufactured in any suitable process including molding such as injection molding, additive manufacturing such as "three-dimensional printing" and/or stereolithography, subtractive processes such as machining, and/or any other process or combination of processes. Housing 404 may include a sensor-bearing surface 412 on or to which one or more electrical components including sensor 408 may be attached. Sensor-bearing surface 412 may be positioned opposite a port aperture as described in further detail below.

Figure 5B:
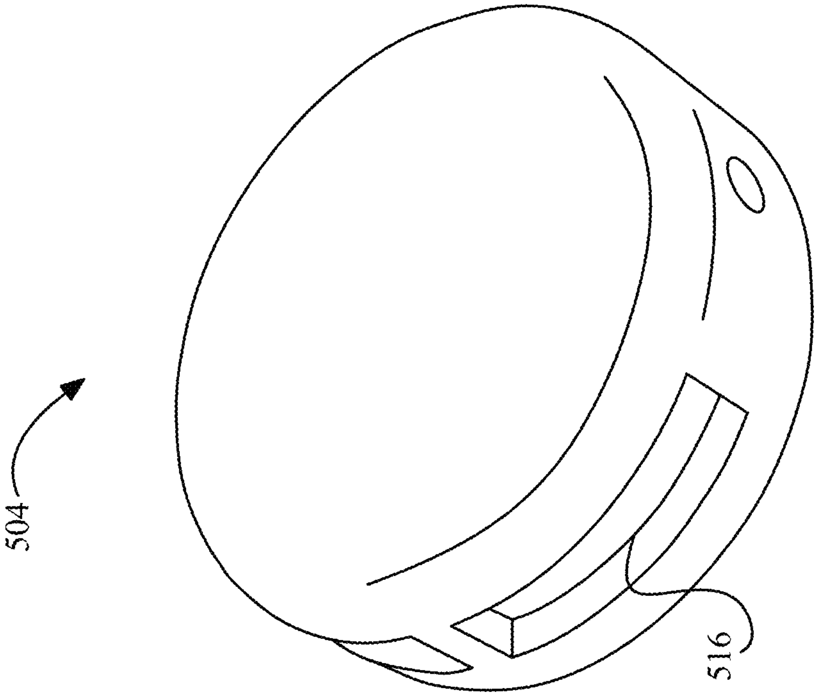
FIG. 5B is a schematic diagram illustrating an exemplary embodiment of a housing.
Figure 5A:
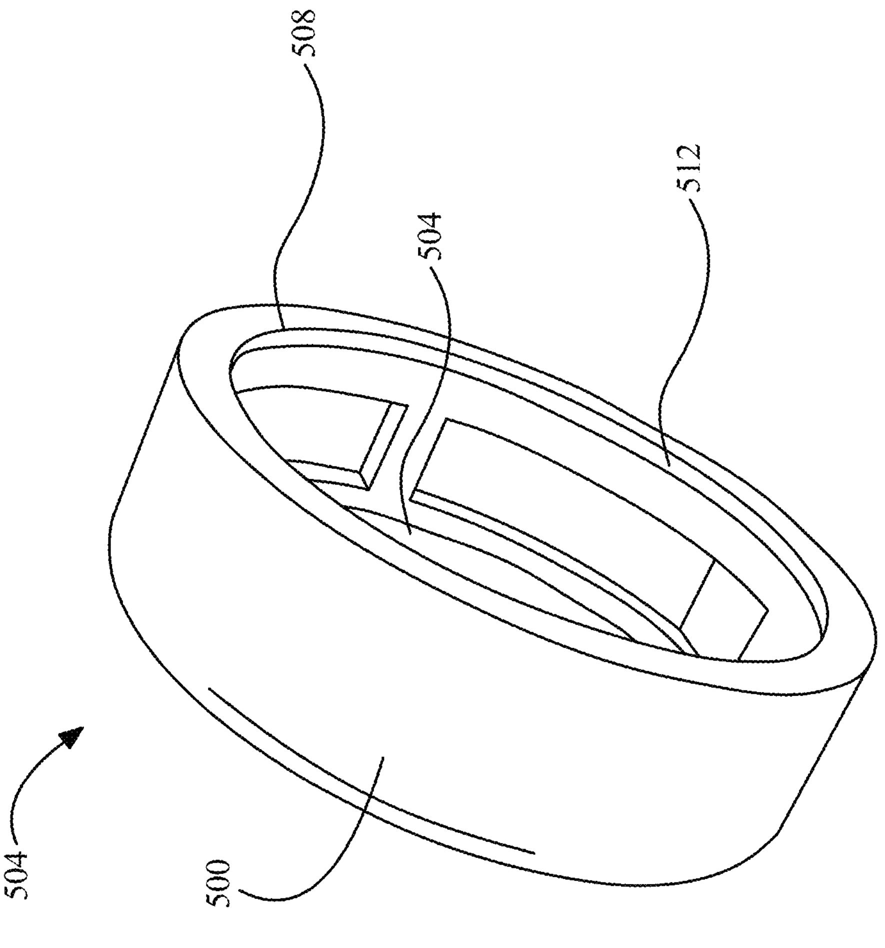
FIG. 5A is a schematic diagram illustrating an exemplary embodiment of a housing.

Referring now to FIG. 5A, a perspective view of an exemplary embodiment of a housing 404 is illustrated. Housing 404 may include an exterior surface 500, an interior surface 504, an interior space surrounded by interior surface 504, and one or more apertures. Housing 404 may have any suitable shape, including a shape of a cap to be placed over a respiratory exhaust port as described in further detail below. Housing 404 may be substantially cylindrical and may have one or more rounded edges. Housing 404 includes a port aperture 508. Port aperture 508 is an aperture that receives exhaled breath from a respiratory exhaust port as described in further detail below, admitting the exhaled breath into interior space of housing 404. Housing 404 further includes a connector 512, which may be located at port aperture 508. A "connector," as used in this disclosure, is a structural feature and/or component that affixes one aperture, opening, port, or the like to another in a way that permits flow of fluids such as liquid and/or gases to flow from one aperture, opening, port, or the like to another. Connector 512 is configured to attach port aperture 508 to exhaust port. Connector 512 may include, without limitation, a rim that fits and/or snaps over a feature of exhaust port to affix port aperture 508 thereto; connector 512 may alternatively or additionally include fastener, such as a bold or screw that inserts through a hole in housing 404 and screws into a reciprocally threaded hole in exhaust port. Connector 512 may include threading around port aperture 508 that engages reciprocal threading at exhaust port. Connector 512 may include and/or be combined with adhesives, sealants, or the like. Connector 512 may permit repeated detachment and reattachment or may effect a permanent connection between port aperture 508 and exhaust port. Persons skilled in the art, upon reviewing the entirety of this disclosure, will be aware of various alternative or additional structures and/or components that may be used for connector 512. Port aperture 508 may be located opposite sensor-bearing surface 412; for instance, sensor-bearing surface 412 may be located on interior surface 504 at a distal end of housing 404, while port aperture 508 may be located at a proximal end of housing 404.

Referring now to FIG. 5B, housing 404 includes at least an ambient aperture 516 connecting to an exterior environment. An "exterior environment," as used in this disclosure, means air that is exterior to an element of mobile respiratory equipment as described below; for instance, where mobile respiratory equipment is a respirator mask, exterior environment may include air outside of the mask and around a person wearing the mask, as opposed to air or gas between the mask and mouth or nose of the person. At least an ambient aperture 516 includes an opening connecting interior space to exterior environment. At least an ambient aperture 516 may permit air to travel freely between interior space and exterior environment.

Figure 6:
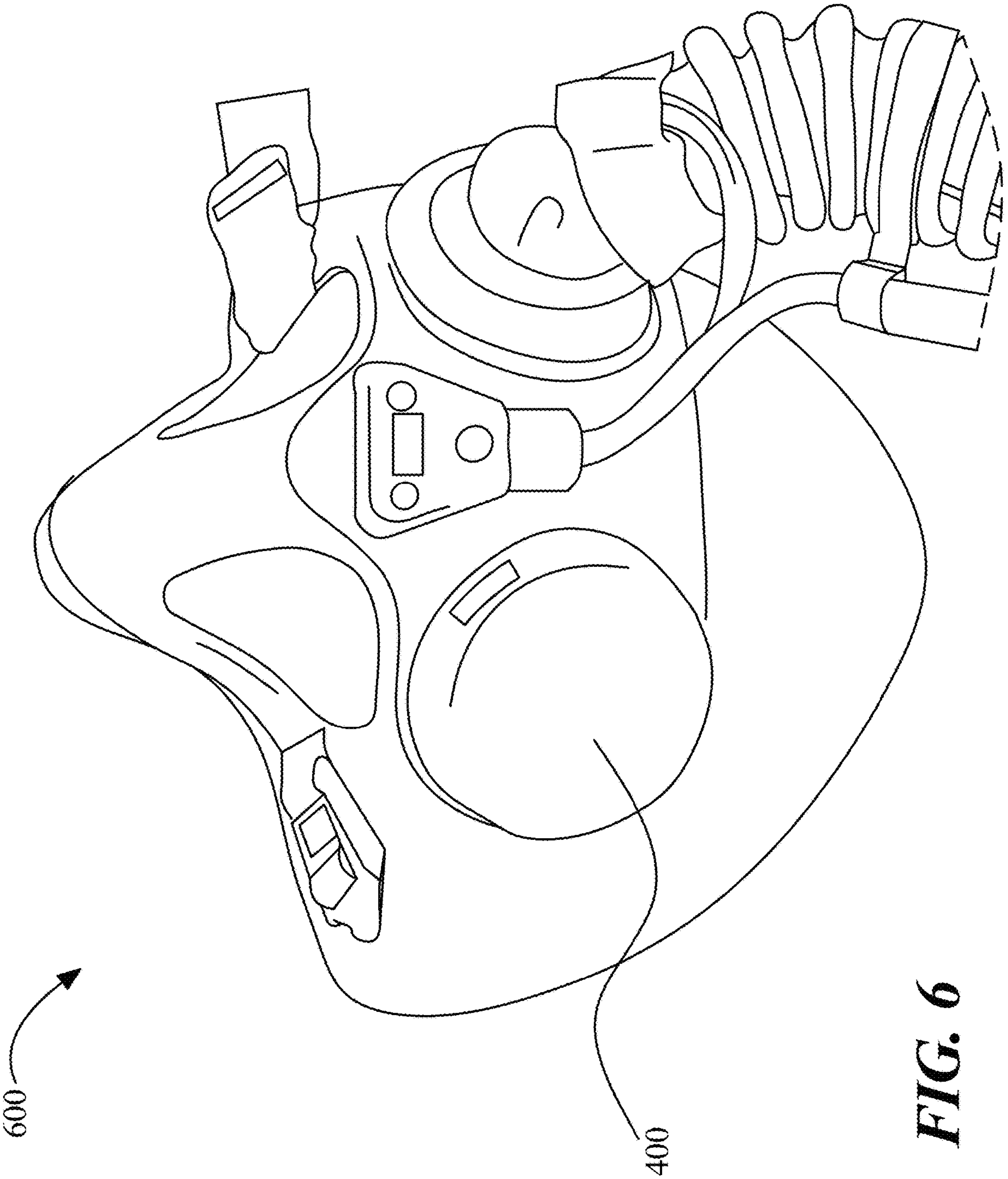
FIG. 6 is a schematic diagram illustrating an exemplary embodiment of a combined exhaled air and environmental gas sensor apparatus.

In an embodiment, and referring now to FIG. 6, housing 404 may be attached to an exhaust port of a mobile respiratory device 600. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill and/or the like.

Still referring to FIG. 6, mobile respiratory device 600 may include, without limitation, a gas mask such as a canister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration.

With continued reference to FIG. 6, an "exhaust port," as used in this disclosure, is an outlet that permits air exhaled by a user to escape from a mobile respiratory device 600. Exhaust port may include a valve such as a check-valve or other one-way valve to prevent air from entering a mobile respiratory device 600 from environment. Exhaust port may include, for instance, an exhale valve of a respirator mask or other such design. Exhaust port may also be an inlet port; for instance, air may be filtered while breathing in through the port and then exhaled, with or without filtering, via a valve at the same port. In operation, housing 404 with port aperture 508 and ambient aperture 516 may form a plenum in which exhaled and ambient air may flow freely by sensor 408, permitting sensation of both breath composition and environmental air composition. Further disclosure related to combined exhaled gas and environmental gas sensor may be found in U.S. patent application Ser. No. 16/933,680, entitled "COMBINED EXHALED AIR AND ENVIRONMENTAL GAS SENSOR APPARATUS," the entirety of which is incorporated herein by reference.

Figure 7:
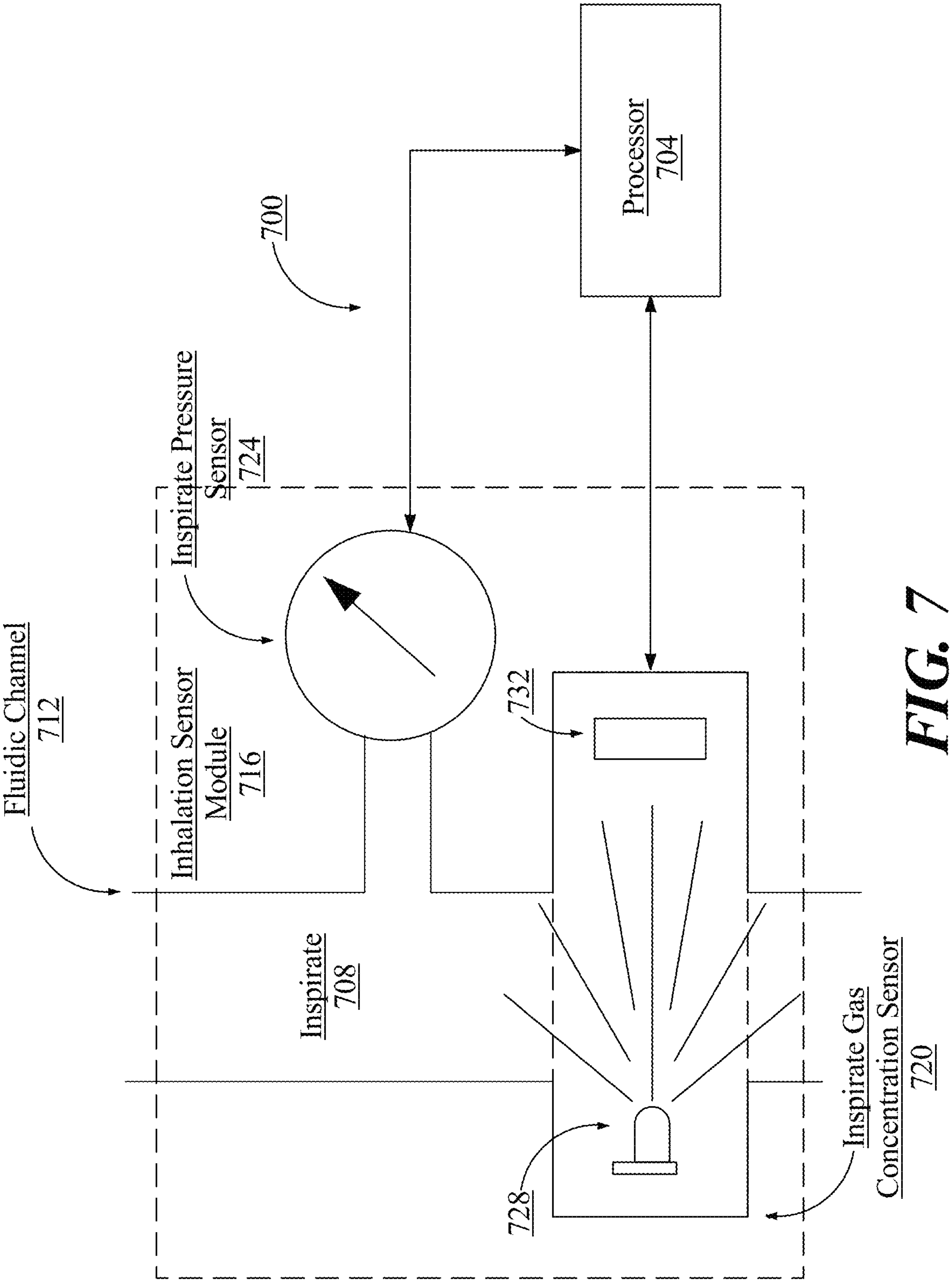
FIG. 7 is a block diagram illustrating an exemplary inhalation sensor module.

In some embodiments, one or more of at least a respiratory sensor 108, circulatory sensor 112, and at least an environmental sensor 120 may include an inspirate sensor. Referring now to FIG. 7, an exemplary inspirate sensor 700 is illustrated. In some embodiments, inspirate sensor 700 may include a processor 704 for making determinations as a function of sensed parameters associated with at least an inspirate 708. in communication with an exemplary inhalation sensor module 708. In some cases, at least a portion of an at least an inspirate 708 is contained within a fluidic channel 712. An exemplary inhalation sensor module 716 is shown in fluid communication with fluidic channel 712. In some cases, inhalation sensor module may include at least a gas concentration sensor 720. In some cases, inhalation sensor module 716 may include at least an inspirate pressure sensor 724. Inspirate gas concentration sensor 720 may include any gas concentration sensor, for instance those described in this application. In some cases, inspirate gas concentration sensor 720 may include an optical gas concentration sensor. Non-limiting optical gas concentration sensors include infrared transmission and/or absorbance spectroscopy type sensors and fluorescence excitation type sensors. Commonly, an optical gas concentration sensor may include a radiation source 728 and a radiation detector 732. In some versions, radiation source 728 may include a light source 728 that may generate a light and illuminate at least a portion of at least an inspirate 708. Radiation source 728 may generate any of a non-limiting list of lights, including coherent light, non-coherent light, narrowband light, broadband light, pulsed light, continuous wave light, pseudo continuous wave light, ultraviolet light, visible light, and infrared light. In some cases, radiation source 728 may include an electromagnetic radiation source that may generate an electromagnetic radiation and irradiate at least a portion of at least an inspirate 708. Radiation source 728 may generate any of a non-limiting list of radiations including radio waves, microwaves, infrared radiation, optical radiation, ultraviolet radiation, X-rays, gamma-rays, and light. Non-limiting examples of radiation sources 728 include lasers, light emitting diodes (LEDs), light emitting capacitors (LECs), flash lamps, antennas, and the like. In some cases, radiation detector 732 may be configured to detect light and/or radiation that has interacted directly or indirectly with at least a portion of at least an inspirate 708. Non-limiting examples of radiation detectors 732 include photodiodes, photodetectors, thermopiles, pyrolytic detectors, antennas, and the like. In some cases, a radiation amount detected by radiation detector 732 may be indicative of a concentration of a particular gas in at least a portion of at least an inspirate 708. For example, in some exemplary embodiments, radiation source 728 may include an infrared light source operating at a wavelength about 4.6 μm and radiation detector may include a photodiode sensitive over a range encompassing 4.6 μm. An exemplary infrared light source may include an LED comprising InAsSb/InAsSbP heterostructures, for example LED46 from Independent Business Scientific Group (IBSG) of Saint Petersburg, Russia. An exemplary infrared detector may include a mercury cadmium telluride photodiode, for example UM-I-6 HgCdTe from Boston Electronics of Brookline, Massachusetts. In some cases, an amount of radiation at least a specific wavelength absorbed, scatter, attenuated, and/or transmitted may be indicative of a gas concentration.

With continued reference to FIG. 7, in some cases, inspirate concentration sensor 720 may include an infrared point sensor. An infrared (IR) point sensor may use radiation passing through a known volume of gas, for example at least an inspirate 708. In some cases, detector 732 may be configured to detect radiation after passing through gas at a specific spectrum. As energy from infrared may be absorbed at certain wavelengths, depending on properties of at least an inspirate 720. For example, carbon monoxide absorbs wavelengths of about 4.2-4.5 μm. In some cases, detected radiation within a wavelength range (e.g., absorption range) may be compared to a wavelength outside of the wavelength range. A difference in detected radiation between these two wavelength ranges may be found to be proportional to a concentration of gas present. In some embodiments, an infrared image sensors may be used for active and/or passive imaging. For active sensing, radiation source 728 may include a coherent light source (e.g., laser) which may be scanned across a field of view of a scene and radiation detector 732 may be configured to detect backscattered light at an absorption wavelength of a specific target gas. In some cases, radiation detector 732 may include an image sensor, for example a two-dimensional array of radiation sensitive devices, for example arranged as pixels. Passive IR imaging sensors may measure spectral changes at each pixel in an image and look for specific spectral signatures that indicate presence and/or concentration of target gases.

With continued reference to FIG. 7, in some cases, inspirate gas concentration sensor 720 may include an oxygen sensor. An exemplary oxygen sensor may include an electro-galvanic sensor. For example, an electro-galvanic oxygen sensor may be used to measure a concentration of oxygen within at least an inspirate 708. In some cases, an electro-galvanic oxygen sensor may include a lead/oxygen galvanic cell, within which oxygen molecules are dissociated and reduced to hydroxyl ions at a cathode. Hydroxyl ions may diffuse through an electrolyte and oxidize a lead anode. A current proportional to a rate of oxygen consumption may be generated when cathode and anode are electrically connected through a resistor. Current may be sensed by known current sensing methods, for example without limitation those described in this disclosure, to produce an electrical signal proportional to a concentration of oxygen, for example oxygen within at least an inspirate. Another exemplary oxygen sensor may include a lambda sensor, for example a zirconia sensor, a wideband zirconia sensor, and/or a titania sensor. A lambda sensor may be configured to sense a quantity of oxygen in a gas (e.g., at least an inspirate 708) relative another gas, for example air within an environment (e.g., cabin air) and transmit an analog voltage correlated to the sensed relative quantity of oxygen. Analog voltage transmitted by a lambda sensor may be processed by any data or signal processing methods discussed herein, for example through amplification and/or analog-to-digital conversion.

In another exemplary embodiment, inspirate concentration sensor 720 may include an optical sensor configured to sense oxygen concentration. In some cases, a chemical film is configured to be in contact with a gas (e.g., at least an inspirate 708). Chemical film may have fluorescence properties which are dependent upon presence and/or concentration of oxygen. Radiation detector 732 may be positioned and configured, such that it is in sensed communication with chemical film. Radiation source 728 may irradiate and/or illuminate chemical film with radiation and/or light having properties (e.g., wavelength, energy, pulse duration, and the like) consistent with exciting fluorescence within the chemical film. In some cases, fluorescence may be at a maximum when there is no oxygen present. For example, oxygen molecules may collide with chemical film and quench photoluminescence resulting from fluorescent excitation. A number of $O_2$ molecules colliding with chemical film may be correlated with a concentration of oxygen within a gas (e.g., inspirate 708). Fluorescence properties as sensed by optical detector 732 may therefore be related to oxygen concentration. Fluorescence properties may include emission duration, fluorescence energy, and the like. In some cases, detected optical signal (fluorescence) to oxygen concentration may not be linear. For instance, an optical oxygen sensor may be most sensitive at low oxygen concentration; that is, sensitivity decreases as oxygen concentration increases, following a known Stern-Volmer relationship. In some cases, an optical oxygen sensor is advantageous as substantially no oxygen may be consumed, during sensing. In some cases, planar optical oxygen sensors (i.e., optodes) may be used to detect a spatial distribution of oxygen concentrations over an area, for example as a two-dimensional image. Based on the same principle, radiation detector 732 may include a digital camera that may be used to capture fluorescence intensities over a specific area.

With continued reference to FIG. 7, inhalation sensor module 716 may include at least an inspirate pressure sensor 724, which is fluidic communication with at least an inspirate 708, for example by way of at least a fluidic channel 712. In some cases, at least an inspirate pressure sensor 716 may be configured to sense and transmit at least an inspirate pressure parameter as a function of a pressure of at least an inspirate 708. In some cases, inhalation pressure sensor 724 may include any type of pressure sensor described in this disclosure. Inhalation pressure sensor 724 may be a force collector type pressure sensor. Alternatively, in some case, inhalation pressure sensor 724 may be a pressure sensor type that does not use force collection. Further disclosure related to inhalation sensor may be found in U.S. patent application Ser. No. 17/333,169, entitled "SYSTEMS AND METHODS FOR INSPIRATE SENSING TO DETERMINE A PROBABILITY OF AN EMERGENT PHYSIOLOGICAL STATE," the entirety of which is incorporated herein by reference.

Figure 8:
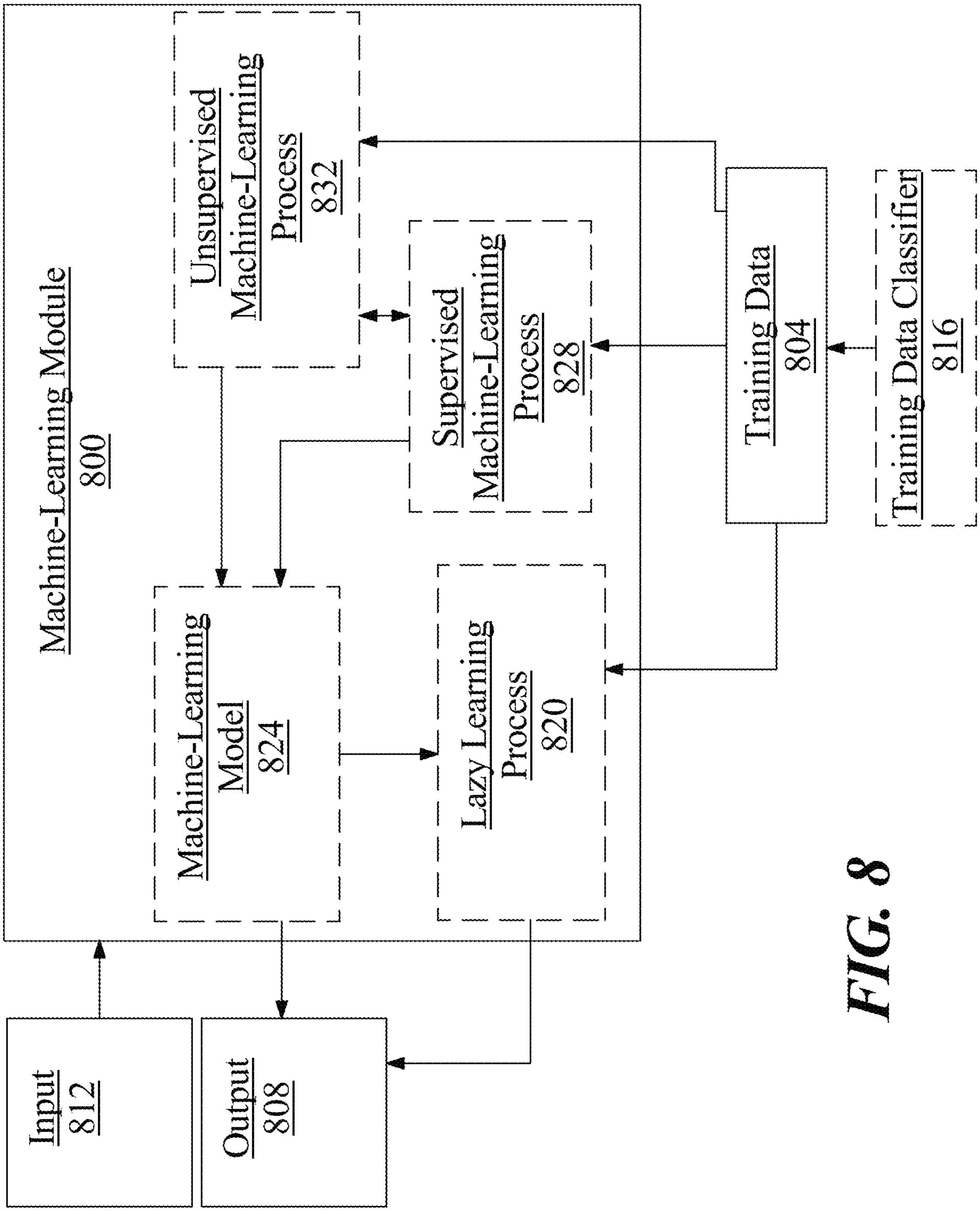
FIG. 8 is a block diagram of an exemplary machine-learning process.

Referring now to FIG. 8, an exemplary embodiment of a machine-learning module 800 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 804 to generate an algorithm that will be performed by a computing device/module to produce outputs 808 given data provided as inputs 812; this is in contrast to a non-machine learning software program where the commands to be executed are determined in advance by a user and written in a programming language.

Still referring to FIG. 8, "training data," as used herein, is data containing correlations that a machine-learning process may use to model relationships between two or more categories of data elements. For instance, and without limitation, training data 804 may include a plurality of data entries, each entry representing a set of data elements that were recorded, received, and/or generated together; data elements may be correlated by shared existence in a given data entry, by proximity in a given data entry, or the like. Multiple data entries in training data 804 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 804 according to various correlations; correlations may indicate causative and/or predictive links between categories of data elements, which may be modeled as relationships such as mathematical relationships by machine-learning processes as described in further detail below. Training data 804 may be formatted and/or organized by categories of data elements, for instance by associating data elements with one or more descriptors corresponding to categories of data elements. As a non-limiting example, training data 804 may include data entered in standardized forms by persons or processes, such that entry of a given data element in a given field in a form may be mapped to one or more descriptors of categories. Elements in training data 804 may be linked to descriptors of categories by tags, tokens, or other data elements; for instance, and without limitation, training data 804 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 8, training data 804 may include one or more elements that are not categorized; that is, training data 804 may not be formatted or contain descriptors for some elements of data. Machine-learning algorithms and/or other processes may sort training data 804 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 804 to be made applicable for two or more distinct machine-learning algorithms as described in further detail below. Training data 804 used by machine-learning module 800 may correlate any input data as described in this disclosure to any output data as described in this disclosure. As a non-limiting illustrative example one or more of at least an environmental parameter, at least a circulation parameter, and/or at least a respiration parameter may be categorized according to user and/or user cohort. In some cases, a machine-learning model may need to be trained using training substantially from only one user. Alternatively or additionally, in some cases, training data may include one or more of at least an environmental parameter, at least a circulation parameter, and/or at least a respiration parameter from a population of users.

Further referring to FIG. 8, training data may be filtered, sorted, and/or selected using one or more supervised and/or unsupervised machine-learning processes and/or models as described in further detail below; such models may include without limitation a training data classifier 816. Training data classifier 816 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 800 may generate a classifier using a classification algorithm, defined as a processes whereby a computing device and/or any module and/or component operating thereon derives a classifier from training data 804. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 8, machine-learning module 800 may be configured to perform a lazy-learning process 820 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 804. Heuristic may include selecting some number of highest-ranking associations and/or training data 804 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 8, machine-learning processes as described in this disclosure may be used to generate machine-learning models 824. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 824 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 824 may be generated by creating an artificial neural network, such as a convolutional neural network comprising an input layer of nodes, one or more intermediate layers, and an output layer of nodes. Connections between nodes may be created via the process of "training" the network, in which elements from a training data 804 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 8, machine-learning algorithms may include at least a supervised machine-learning process 828. At least a supervised machine-learning process 828, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 804. Persons skilled in the art, upon reviewing the entirety of this disclosure, will be aware of various possible variations of at least a supervised machine-learning process 828 that may be used to determine relation between inputs and outputs. Supervised machine-learning processes may include classification algorithms as defined above.

Further referring to FIG. 8, machine learning processes may include at least an unsupervised machine-learning processes 832. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 8, machine-learning module 800 may be designed and configured to create a machine-learning model 824 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 8, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 9:
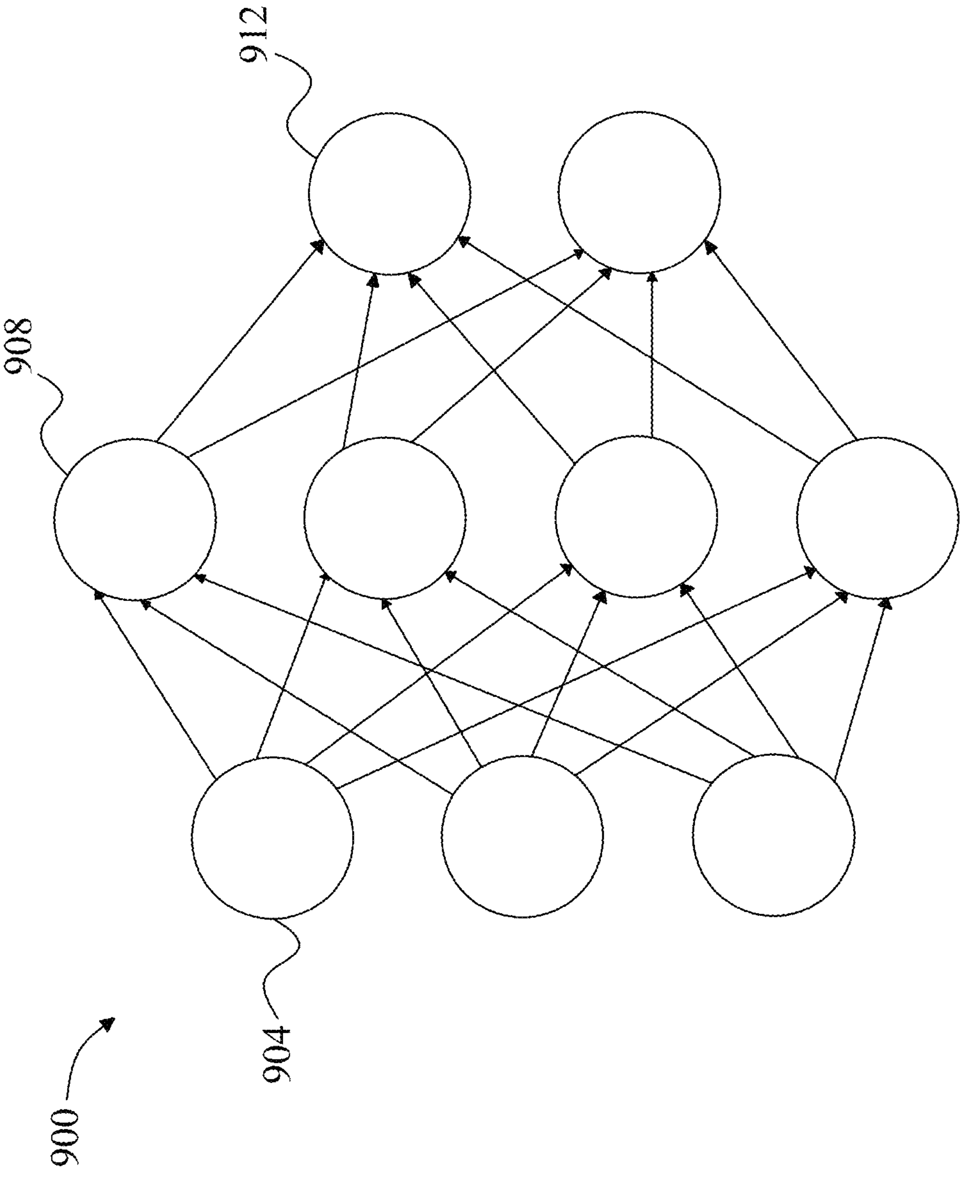
FIG. 9 is a schematic diagram of an exemplary embodiment of a neural network.

Referring now to FIG. 9 an exemplary embodiment of neural network 900 is illustrated. Neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 904, one or more intermediate layers 908, and an output layer of nodes 912. Connections between nodes may be created via the process of "training" the network, in which elements from a training dataset are applied to input nodes 904, a suitable training algorithm (such as Levenberg-Marquardt, conjugate gradient, simulated annealing, or other algorithms) is then used to adjust the connections and weights between nodes in adjacent layers 908 of the neural network to produce the desired values at output nodes 912. This process is sometimes referred to as deep learning.

Figure 10:
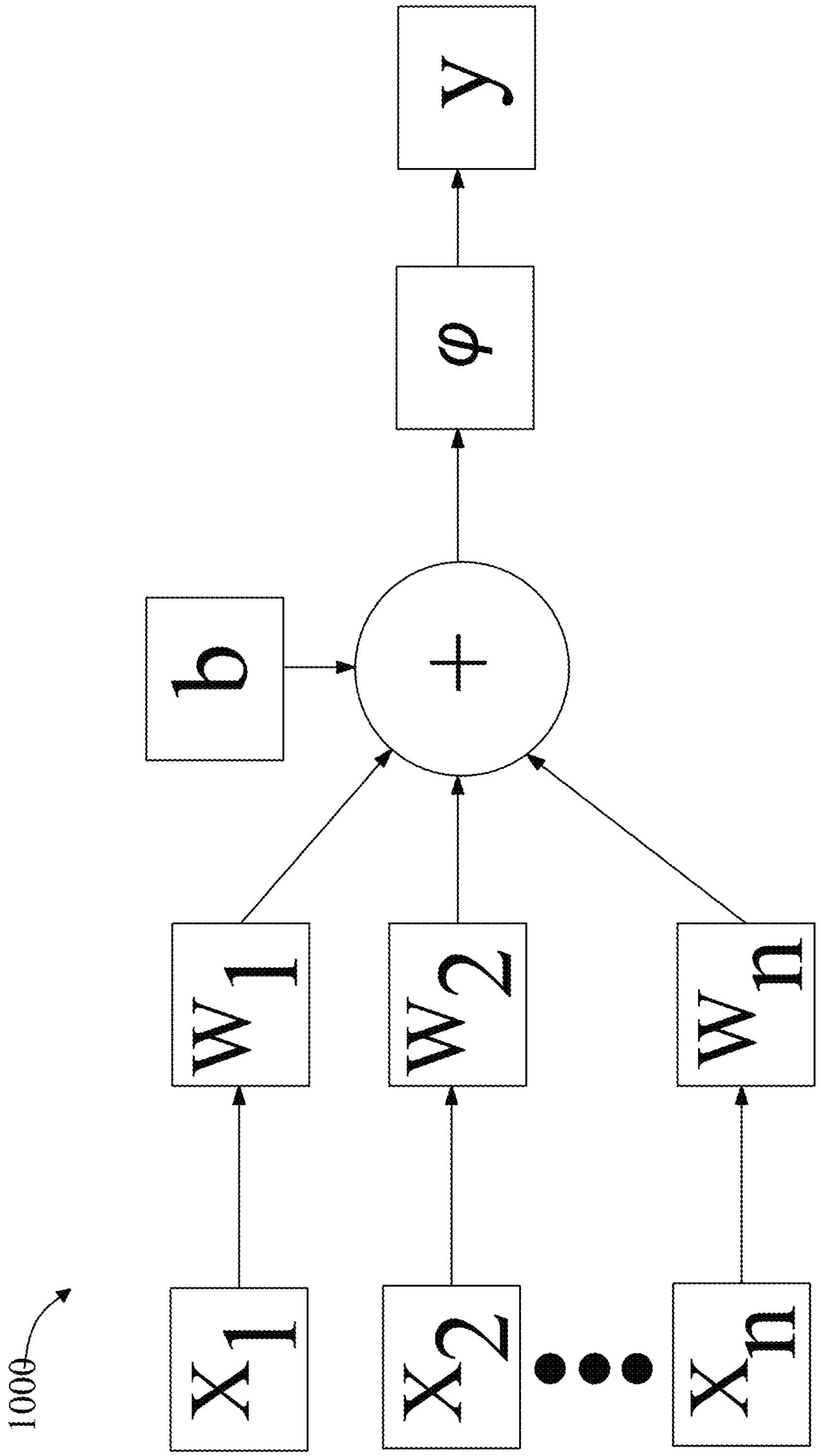
FIG. 10 is a schematic diagram of an exemplary embodiment of a node of a neural network.

Referring now to FIG. 10, an exemplary embodiment of a node 1000 of a neural network is illustrated. A node 1000 may include, without limitation a plurality of inputs $x_i$ that may receive numerical values from inputs to a neural network containing the node and/or from other nodes. Node 1000 may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 10, a neural network may receive one or more of at least an environmental parameter, at least a circulation parameter, and/or at least a respiration parameter as inputs and output one or more of a condition and/or an imminent loss of consciousness event. Alternatively or additionally in some cases, a neural network may receive one or more of at least an environmental parameter, at least a circulation parameter, and/or at least a respiration parameter as inputs and output a confidence metric representing a probability of classification to a predetermined class, for instance condition and/or imminent loss of consciousness event, according to weights $w_i$ that are derived using machine-learning processes as described in this disclosure.

Referring again to FIG. 1, In some embodiments, processor 104 may be configured to modify a training set in response to one or more of at least an environmental parameter, at least a circulation parameter, and/or at least a respiration parameter correlated to a condition and/or an imminent loss of consciousness event; where the condition or the imminent loss of consciousness event may represent an actual known occurrence that is related to a user. For example, processor 104 may, in some cases, retrain a machine-learning model using one or more of at least an environmental parameter, at least a circulation parameter, and/or at least a respiration parameter correlated to a condition and/or an imminent loss of consciousness event. In some embodiments, processor 104 may be configured to classify at least one of a condition and an imminent loss of consciousness state and determine a confidence metric. For example, in some exemplary embodiments confidence metric may be a floating-point number within a prescribed range, such as without limitation 0 to 1, with each end of the prescribed range representing an extreme representation, such as without limitation substantially no confidence and substantially absolute confidence, respectively. In some cases, confidence output may represent a relationship between a result of filtering and/or classifying. Confidence metric may be determined by one more comparisons algorithms, such as without limitation a fuzzy set comparison. For example, in some exemplary embodiments a fuzzy set comparison may be employed to compare a probabilistic outcome with a membership function derived to represent at least a threshold used for classification.

Figure 11:
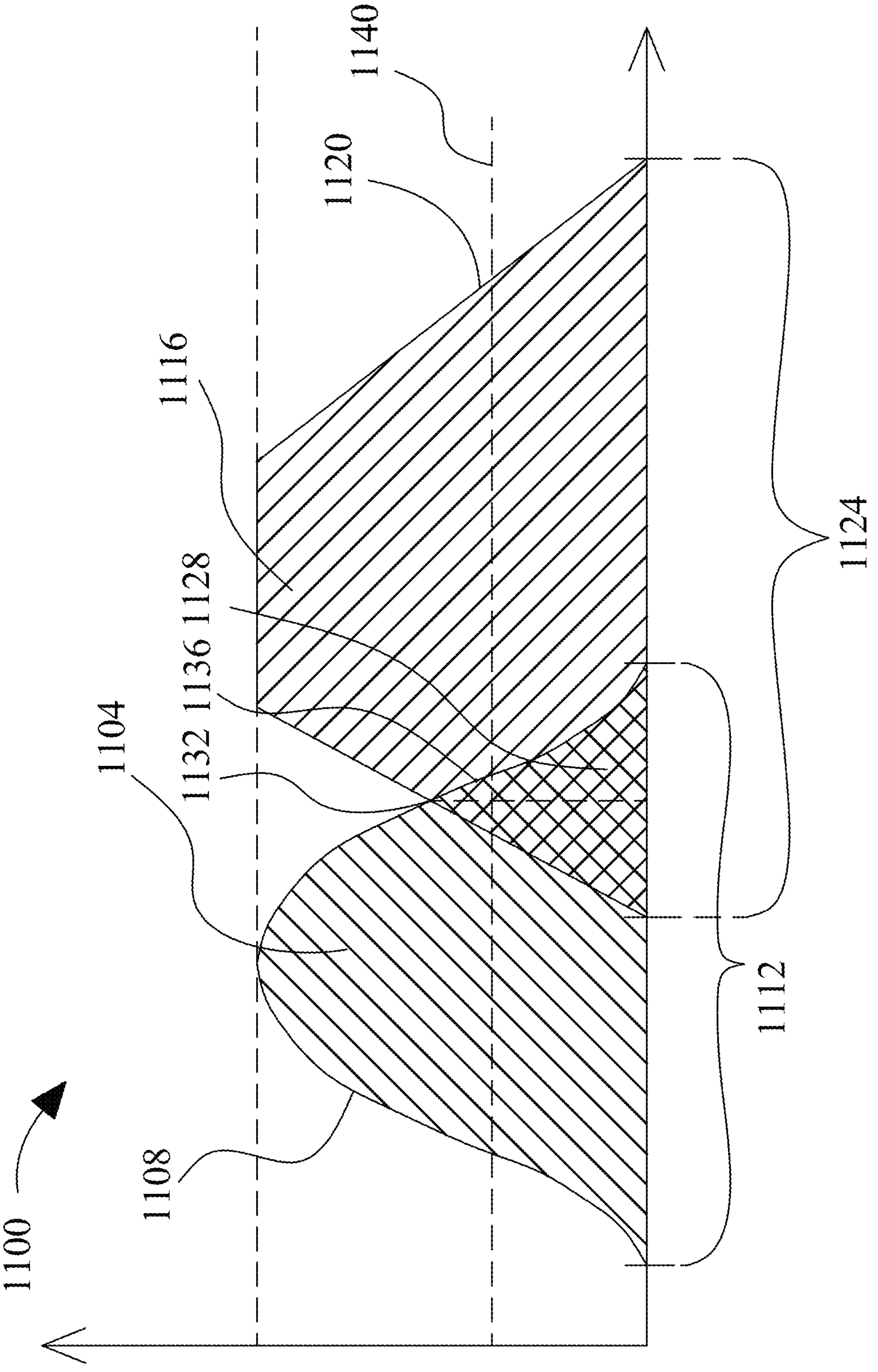
FIG. 11 is a graph representing an exemplary embodiment of a fuzzy set comparison.

Referring to FIG. 11, an exemplary embodiment of fuzzy set comparison 1100 is illustrated. A first fuzzy set 1104 may be represented, without limitation, according to a first membership function 1108 representing a probability that an input falling on a first range of values 1112 is a member of the first fuzzy set 1104, where the first membership function 1108 has values on a range of probabilities such as without limitation the interval [0,1], and an area beneath the first membership function 1108 may represent a set of values within first fuzzy set 1104. Although first range of values 1112 is illustrated for clarity in this exemplary depiction as a range on a single number line or axis, first range of values 1112 may be defined on two or more dimensions, representing, for instance, a Cartesian product between a plurality of ranges, curves, axes, spaces, dimensions, or the like. First membership function 1108 may include any suitable function mapping first range 1112 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \dfrac{x-a}{b-a}, \text{ for } a \le x < b \\ \dfrac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 11, first fuzzy set 1104 may represent any value or combination of values as described above, including output from one or more algorithms, one or more machine-learning models and one or more of at least an environmental parameter, at least a circulation parameter, and/or at least a respiration parameter from a sensor 108, 112, and 120, a predetermined class, such as without limitation a condition and/or an imminent loss of consciousness. A second fuzzy set 1116, which may represent any value which may be represented by first fuzzy set 1104, may be defined by a second membership function 1120 on a second range 1124; second range 1124 may be identical and/or overlap with first range 1112 and/or may be combined with first range via Cartesian product or the like to generate a mapping permitting evaluation overlap of first fuzzy set 1104 and second fuzzy set 1116. Where first fuzzy set 1104 and second fuzzy set 1116 have a region 1128 that overlaps, first membership function 1108 and second membership function 1120 may intersect at a point 1132 representing a probability, as defined on probability interval, of a match between first fuzzy set 1104 and second fuzzy set 1116. Alternatively or additionally, a single value of first and/or second fuzzy set may be located at a locus 1136 on first range 1112 and/or second range 1124, where a probability of membership may be taken by evaluation of first membership function 1108 and/or second membership function 4110 at that range point. A probability at 1128 and/or 1132 may be compared to a threshold 1140 to determine whether a positive match is indicated. Threshold 1140 may, in a non-limiting example, represent a degree of match between first fuzzy set 1104 and second fuzzy set 1116, and/or single values therein with each other or with either set, which is sufficient for purposes of the matching process; for instance, threshold may indicate a sufficient degree of overlap between an output from one or more machine-learning models and/or a biofeedback signal and a predetermined class, such as without limitation a user state, for combination to occur as described above. Alternatively or additionally, each threshold may be tuned by a machine-learning and/or statistical process, for instance and without limitation as described in further detail below.

Further referring to FIG. 11, in an embodiment, a degree of match between fuzzy sets may be used to classify one or more of at least an environmental parameter, at least a circulation parameter, and/or at least a respiration parameter with a condition and/or an imminent loss of consciousness. For instance, if one or more of at least an environmental parameter, at least a circulation parameter, and/or at least a respiration parameter has a fuzzy set matching a condition and/or imminent loss of consciousness fuzzy set by having a degree of overlap exceeding a threshold, processor 104 may classify the one or more of at least an environmental parameter, at least a circulation parameter, and/or at least a respiration parameter as belonging to the condition and/or imminent loss of consciousness. Where multiple fuzzy matches are performed, degrees of match for each respective fuzzy set may be computed and aggregated through, for instance, addition, averaging, or the like, to determine an overall degree of match.

Still referring to FIG. 11, in an embodiment, one or more of at least an environmental parameter, at least a circulation parameter, and/or at least a respiration parameter may be compared to multiple user state fuzzy sets. For instance, one or more of at least an environmental parameter, at least a circulation parameter, and/or at least a respiration parameter may be represented by a fuzzy set that is compared to each of the multiple condition and/or imminent loss of consciousness fuzzy sets; and a degree of overlap exceeding a threshold between the one or more of at least an environmental parameter, at least a circulation parameter, and/or at least a respiration parameter fuzzy set and any of the multiple condition and/or imminent loss of consciousness fuzzy sets may cause processor 104 to classify the one or more of at least an environmental parameter, at least a circulation parameter, and/or at least a respiration parameter as belonging to a condition and/or an imminent loss of consciousness. For instance, in one embodiment there may be two condition fuzzy sets, representing respectively hypoxia and hypocapnia. Hypoxia may have a hypoxia fuzzy set; Hypocapnia may have a hypocapnia fuzzy set; and one or more of at least an environmental parameter, at least a circulation parameter, and/or at least a respiration parameter may have a parameter fuzzy set. Processor 104, for example, may compare a parameter fuzzy set with each of hypoxia fuzzy set and hypocapnia fuzzy set, as described above, and classify one or more of at least an environmental parameter, at least a circulation parameter, and/or at least a respiration parameter to either, both, or neither of hypoxia or hypocapnia conditions. Machine-learning methods as described throughout may, in a non-limiting example, generate coefficients used in fuzzy set equations as described above, such as without limitation x, c, and σ of a Gaussian set as described above, as outputs of machine-learning methods. Likewise, one or more of at least an environmental parameter, at least a circulation parameter, and/or at least a respiration parameter may be used indirectly to determine a fuzzy set, as parameter fuzzy set may be derived from outputs of one or more machine-learning models and/or algorithms that take the one or more of at least an environmental parameter, at least a circulation parameter, and/or at least a respiration parameter directly or indirectly as inputs.

Figure 12:
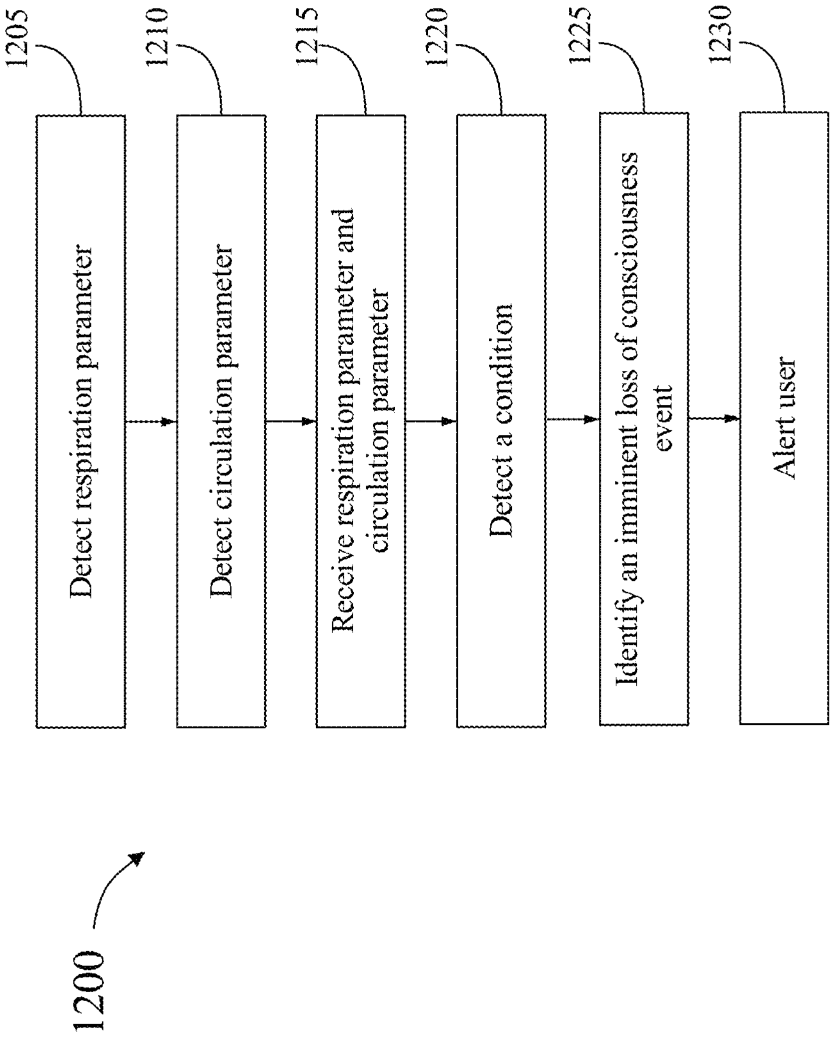
FIG. 12 is a flow diagram of an exemplary method of detecting imminent loss of consciousness.

Referring now to FIG. 12, a flow diagram illustrates an exemplary method 1200 of detecting imminent loss of consciousness. At step 1205, method 1200 may include detecting, using at least a respiratory sensor, a respiration parameter associated with a user. Respiratory sensor may include any sensor described in this disclosure, including with reference to FIGS. 1-11. User may include any user described in this disclosure, including with reference to FIGS. 1-11.

With continued reference to FIG. 12, at step 1210, method 1200 may include detecting, using at least a circulatory sensor, a circulation parameter associated with user. Circulatory sensor may include any sensor described in this disclosure, including with reference to FIGS. 1-11. In some embodiments, at least a circulatory sensor may include a near-infrared spectroscopy sensor.

With continued reference to FIG. 12, at step 1215, method 1200 may include receiving, using at least a processor, at least a respiration parameter and at least a circulation parameter. Processor may include any processor described in this disclosure, including with reference to FIGS. 1-11. In some embodiments, at least a respiratory sensor may include at least an inhalation sensor. In some embodiments, at least a respiratory sensor may include at least an exhalation sensor.

With continued reference to FIG. 12, at step 1220, method 1200 may include detecting, using at least a processor, a condition associated with user as a function of at least a respiration parameter and at least a circulation parameter. Condition may include any condition described in this disclosure, including with reference to FIGS. 1-11. In some embodiments, condition may include hypoxia and/or hypocapnia.

With continued reference to FIG. 12, at step 1225, method 1200 may include identifying, using at least a processor, an imminent loss of consciousness event associated with user as a function of at least a respiration parameter and at least a circulation parameter. Imminent loss of consciousness event may include any imminent loss of consciousness event described in this disclosure, including with reference to FIGS. 1-11.

With continued reference to FIG. 12, at step 1230, method 1200 may include alerting, using at least a user interface, user as a function of imminent loss of consciousness event. User interface may include any user interface described in this disclosure, including with reference to FIGS. 1-11. In some embodiments, method 1200 may additionally include generating, using an audio system, auditory coaching to user as a function of imminent loss of consciousness event. Audio system may include any audio system described in this disclosure, including with reference to FIGS. 1-1. Auditory coaching may include any auditory coaching described in this disclosure, including with reference to FIGS. 1-11.

Still referring to FIG. 12, in some embodiments, method 1200 may additionally include detecting, using a master circulatory sensor, a master circulation parameter, detecting, using a slave circulatory sensor, a slave circulation parameter, and merging, using at least a processor, at least a circulation parameter as a function of the master circulation parameter and the slave circulation parameter. Master circulation parameter may include any master parameter described in this disclosure, including with reference to FIGS. 1-11. Slave circulation parameter may include any slave circulation parameter described in this disclosure, including with reference to FIGS. 1-11.

Still referring to FIG. 12, in some embodiments, method 1200 may additionally include detecting, using at least a motion sensor, at least a motion parameter, receiving, using at least a processor, the at least a motion parameter, detecting, using the at least a processor, the condition as a function of the at least a motion parameter, and identifying, using at least a processor, the imminent loss of consciousness event as a function of the at least a motion parameter. In some cases, motion sensor may include at least an environmental sensor. Motion sensor may include any sensor described in this disclosure, including with reference to FIGS. 1-11. In some cases, condition may include G-induced loss of consciousness.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
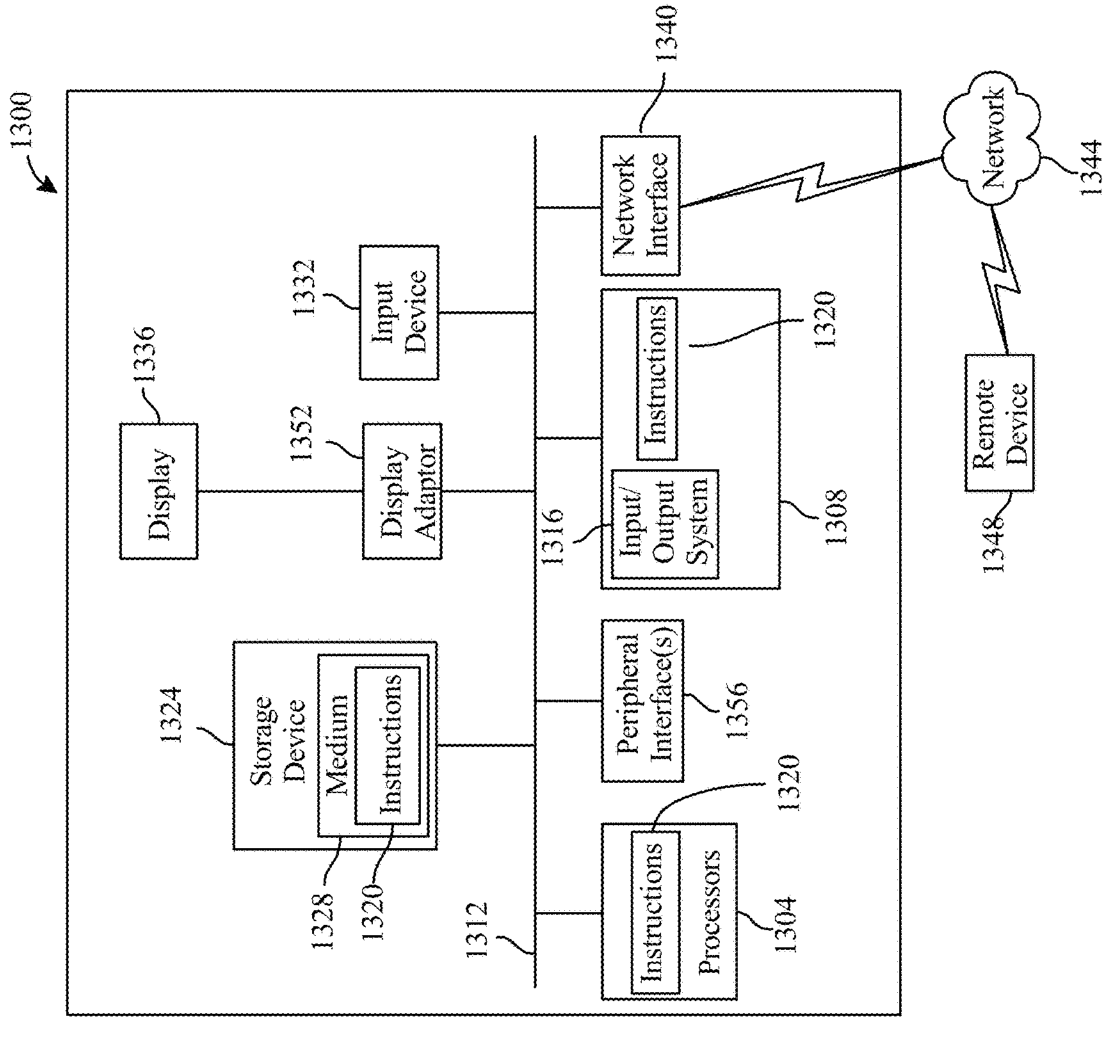
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for detecting imminent loss of consciousness, the system comprising:

at least a respiratory sensor configured to detect a respiration parameter associated with a user;

at least a circulatory sensor configured to detect a circulation parameter associated with the user, wherein the circulation parameter comprises a pulse rate;

an inspirate sensor configured to detect a fluid parameter associated with a fluid;

an inhalation sensor module comprising at least one sensor in communication with the inspirate sensor;

wherein the inspirate sensor and the inhalation sensor module are operable to be configured for fluidic communication;

at least a processor configured to:

receive the at least a respiration parameter and the at least a circulation parameter;

generate a first trend analysis for the at least a respiration parameter and a second trend analysis for the pulse rate;

compare the first trend analysis of the at least a respiration parameter to the second trend analysis of the pulse rate;

make at least one determination as a function of at least one of the detected fluid parameter; and identify an imminent loss of consciousness event associated with the user as a function of the comparison, wherein identifying the imminent loss of consciousness event comprises determining that the comparison satisfies a threshold condition continuously for at least a predetermined duration; and at least a user interface configured to alert the user as a function of the imminent loss of consciousness event wherein the user interface further comprises a bone-conducting transducer.

2. The system of claim 1, wherein the at least a circulatory sensor comprises:

a master circulatory sensor configured to detect a master circulation parameter; and a slave circulatory sensor configured to detect a slave circulation parameter; and wherein, the at least a processor is further configured to merge the circulation parameter as a function of the master circulation parameter and the slave circulation parameter.

3. The system of claim 1, wherein the at least a circulatory sensor comprises a near-infrared spectroscopy sensor.

4. The system of claim 1, wherein the at least a respiratory sensor comprises one or more of at least an inhalation sensor and at least an exhalation sensor.

5. The system of claim 1, wherein the at least a processor is further configured to detect a condition associated with the user as a function of the at least a respiration parameter and the at least a circulation parameter.

6. The system of claim 1, wherein:

the system further comprises at least a motion sensor configured to detect at least a motion parameter; and the at least a processor is further configured to:

receive the at least a motion parameter;

detect a condition as a function of the at least a motion parameter; and identify the imminent loss of consciousness event as a function of the at least a motion parameter.

7. The system of claim 6, wherein the condition includes G-induced loss of consciousness.

8. The system of claim 6, wherein the condition includes hypoxia.

9. The system of claim 6, wherein the condition includes hypocapnia.

10. The system of claim 1, wherein alerting the user comprises:

classifying, using the at least a processor, a condition associated with the user from a plurality of candidate conditions based on the comparison and the at least one determination;

selecting, using the at least a processor, an alert type for the bone-conducting transducer as a function of the classified condition; and alerting, using the at least a user interface, the user as a function of the imminent loss of consciousness event and the alert type, wherein the at least a user interface comprises an audio system.

11. The system of claim 1, wherein at least the first trend analysis includes a moving average converging/diverging (MACD) value and wherein the moving average converging/diverging (MACD) value further comprises a short-term trend associated with the imminent loss of consciousness event and a long-term trend associated with the imminent loss of consciousness event.

12. A method of detecting imminent loss of consciousness, the method comprising:

detecting, using at least a respiratory sensor, a respiration parameter associated with a user;

detecting, using at least a circulatory sensor, a circulation parameter associated with the user, wherein the circulation parameter comprises a pulse rate;

detecting, using an inspirate sensor, a fluid parameter associated with a fluid, wherein the inspirate sensor and an inhalation sensor module are operable to be configured for fluidic communication, wherein the inhalation sensor module comprises at least one sensor in communication with the inspirate sensor;

receiving, using at least a processor, the at least a respiration parameter and the at least a circulation parameter;

generating, using the at least a processor, a first trend analysis for the at least a respiration parameter and a second trend analysis for the pulse rate;

comparing, using the at least a processor, the first trend analysis of the at least a respiration parameter to the second trend analysis of the pulse rate;

making, using the at least a processor, at least one determination as a function of at least one of the detected fluid parameter;

identifying, using the at least a processor, an imminent loss of consciousness event associated with the user as a function of the comparison, wherein identifying the imminent loss of consciousness event comprises determining that the comparison satisfies a threshold condition continuously for at least a predetermined duration; and alerting, using at least a user interface, the user as a function of the imminent loss of consciousness event wherein the user interface further comprises a bone-conducting transducer.

13. The method of claim 12, further comprising:

detecting, using a master circulatory sensor, a master circulation parameter;

detecting, using a slave circulatory sensor, a slave circulation parameter; and merging, using the at least a processor, the circulation parameter as a function of the master circulation parameter and the slave circulation parameter.

14. The method of claim 12, wherein the at least a circulatory sensor comprises a near-infrared spectroscopy sensor.

15. The method of claim 12, wherein the at least a respiratory sensor comprises one or more of at least an inhalation sensor and at least an exhalation sensor.

16. The method of claim 12, further comprising detecting, using the at least a processor, a condition associated with the user as a function of the at least a respiration parameter and the at least a circulation parameter.

17. The method of claim 12, further comprising:

detecting, using at least a motion sensor, at least a motion parameter;

receiving, using the at least a processor, the at least a motion parameter;

detecting, using the at least a processor, a condition as a function of the at least a motion parameter; and identifying, using at least a processor, the imminent loss of consciousness event as a function of the at least a motion parameter.

18. The method of claim 17, wherein the condition includes G-induced loss of consciousness.

19. The method of claim 17, wherein the condition includes hypoxia.

20. The method of claim 17, wherein the condition includes hypocapnia.

21. The method of claim 12, wherein generating the alert comprises:

classifying, using the at least a processor, a condition associated with the user from a plurality of candidate conditions based on the comparison and the at least one determination;

selecting, using the at least a processor, an alert type for the bone-conducting transducer as a function of the classified condition; and alerting, using the at least a user interface, the user as a function of the imminent loss of consciousness event and the alert type, wherein the at least a user interface comprises an audio system.

22. The method of claim 12, wherein at least the first trend analysis includes a moving average converging/diverging (MACD) value and wherein the moving average converging/diverging (MACD) value further comprises a short-term trend associated with the imminent loss of consciousness event and a long-term trend associated with the imminent loss of consciousness event.

* * * * *